US009351880B2

(12) United States Patent
McCulloch et al.

(10) Patent No.: US 9,351,880 B2
(45) Date of Patent: *May 31, 2016

(54) GOGGLE WITH EASILY INTERCHANGEABLE LENS THAT IS ADAPTABLE FOR HEATING TO PREVENT FOGGING

(71) Applicant: ABOMINABLE LABS, LLC, Lake Oswego, OR (US)

(72) Inventors: David C. McCulloch, Lake Oswego, OR (US); Jack C. Cornelius, Lake Oswego, OR (US); Toren P. B. Orzeck, Portland, OR (US)

(73) Assignee: Abominable Labs, LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/918,431

(22) Filed: Oct. 20, 2015

(65) Prior Publication Data

US 2016/0051411 A1 Feb. 25, 2016

Related U.S. Application Data

(62) Division of application No. 13/587,908, filed on Aug. 16, 2012.

(60) Provisional application No. 61/548,253, filed on Oct. 18, 2011.

(51) Int. Cl.
*A61F 9/00* (2006.01)
*A61F 9/02* (2006.01)
*A42B 3/24* (2006.01)

(52) U.S. Cl.
CPC . *A61F 9/029* (2013.01); *A42B 3/24* (2013.01); *A42B 3/245* (2013.01); *A61F 9/025* (2013.01); *A61F 9/027* (2013.01); *A61F 9/028* (2013.01)

(58) Field of Classification Search
CPC ............... A42B 3/24; A42B 3/245; A63B 33/00–2033/008; A61F 9/029; A61F 9/027; A61F 9/028
USPC ............ 2/429, 430, 432, 435, 436, 438, 441, 2/443, 449
See application file for complete search history.

(56) References Cited

U.S. PATENT DOCUMENTS

| 3,050,736 A | 8/1962 | Malcom, Jr. |
| 4,209,234 A | 6/1980 | McCooeye |

(Continued)

FOREIGN PATENT DOCUMENTS

CN 2397631 Y 9/2000

*Primary Examiner* — Danny Worrell
*Assistant Examiner* — Khaled Annis
(74) *Attorney, Agent, or Firm* — Howard Russell

(57) ABSTRACT

Anti-fog, interchangeable-lens goggle adapted for use with a battery comprising: a body with a flexible posterior portion for engaging a user's face and an anterior portion; a lens having a resistive anti-fog element thereon, the lens adapted for engaging the anterior portion of the body; an engagement mechanism for releasably interconnecting the lens and the body; an interconnection mechanism depending from the body adapted for detachably interconnecting the heating element of the lens and the battery, the interconnection means operable or integral with the engagement mechanism such that interconnecting the heating element of the lens with the battery also reinforces interconnecting of the lens with the semi-rigid anterior portion of the body; and a strap adapted for holding the goggle on one of a user's head and helmet.

15 Claims, 18 Drawing Sheets

(56) References Cited

U.S. PATENT DOCUMENTS

| | | | |
|---|---|---|---|
| 4,638,728 A | 1/1987 | Elenewski | |
| 4,868,929 A | 9/1989 | Curcio | |
| 4,942,629 A | 7/1990 | Stadlmann | |
| 5,459,533 A | 10/1995 | McCooeye et al. | |
| 5,471,036 A | 11/1995 | Sperbeck | |
| 5,617,588 A | 4/1997 | Canavan et al. | |
| 5,815,235 A | 9/1998 | Runckel | |
| 6,701,537 B1 | 3/2004 | Stamp | |
| 6,704,944 B2 | 3/2004 | Kawainshi et al. | |
| 7,648,234 B2 | 1/2010 | Welchel et al. | |
| 7,810,174 B2 | 10/2010 | Matera | |
| 7,856,673 B2 | 12/2010 | Reed | |
| 8,893,314 B2 | 11/2014 | Chen et al. | |
| 2002/0157175 A1 | 10/2002 | Dondero | |
| 2006/0048289 A1 | 3/2006 | Shiue | |
| 2008/0290081 A1 | 11/2008 | Biddell | |
| 2008/0316421 A1 | 12/2008 | Wang | |
| 2009/0151057 A1 | 6/2009 | Lebel et al. | |
| 2011/0225709 A1 | 9/2011 | Saylor et al. | |

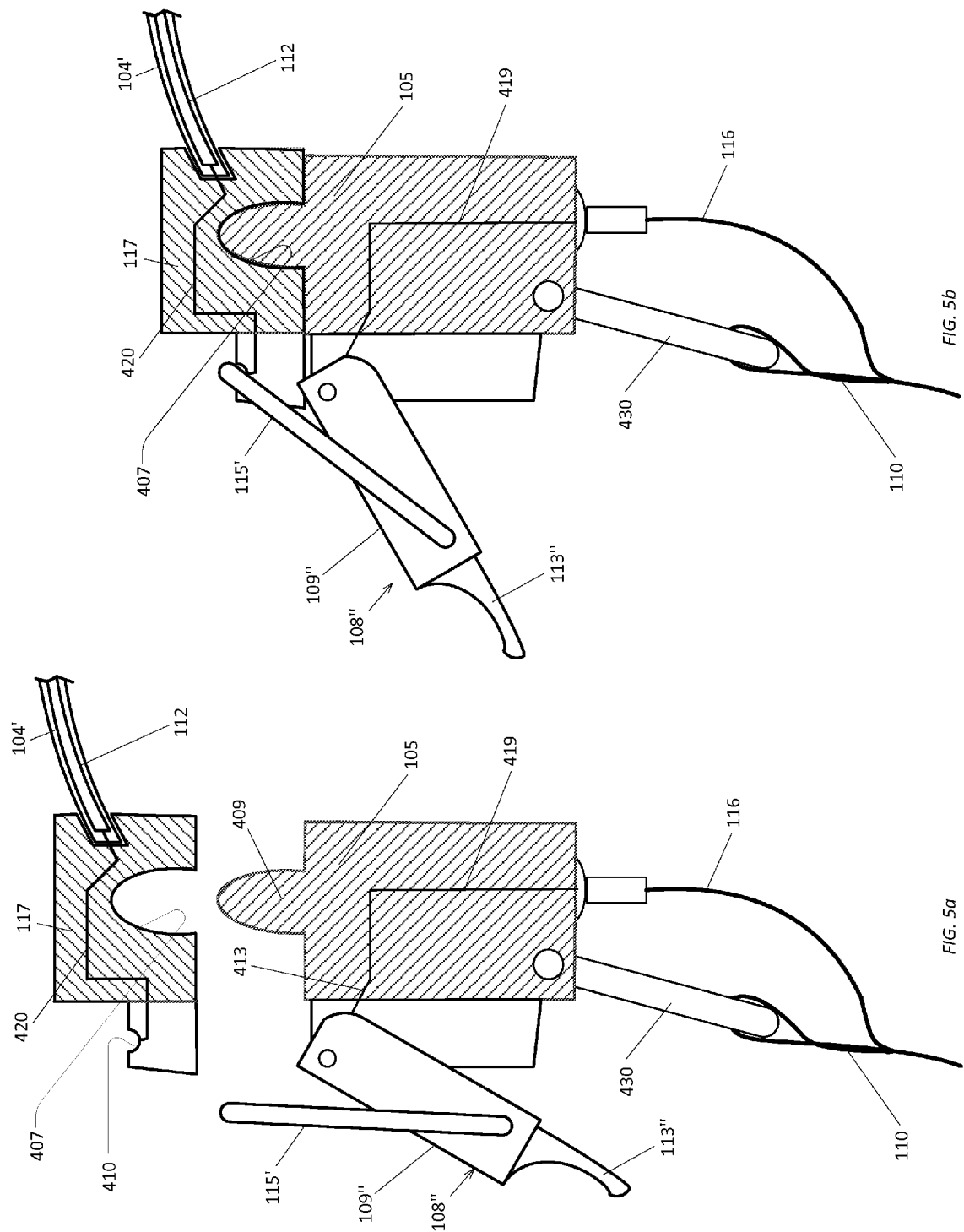

GOGGLE WITH EASILY INTERCHANGEABLE LENS THAT IS ADAPTABLE FOR HEATING TO PREVENT FOGGING

CROSS-REFERENCE

This patent application is a divisional patent application and claims the benefit and priority of U.S. patent application Ser. No. 13/587,908 filed Aug. 16, 2012, which claims the benefit and priority of U.S. Provisional Patent Application Ser. No. 61/548,253 filed Oct. 18, 2011. This application incorporates patent application Ser. No. 13/587,908 herein by this reference.

FIELD OF INVENTION

This invention relates generally to goggles and more particularly to goggles that have easily interchangeable lenses for enabling adaptation to varying weather, lighting and goggle fogging conditions.

BACKGROUND OF INVENTION

Goggle Construction Generally

Sport goggles, such as are often used for skiing, cycling, snow-boarding, motorcycle and ATV riding, paint-balling, or standard-issue military goggles used primarily for military ground operations, typically have comprised a plastic frame or body and a clear plastic, or polycarbonate, see-through lens. Sometimes the plastic body has further been comprised of an anterior body interconnected to a posterior body, the foremost portion of the anterior body being designed for attachment to, carrying and positioning of the lens a comfortable distance from a user's eyes. The posterior body has comprised a foam rubber interface on the most posterior portion thereof for comfortable positioning of the body on the user's face around and defining the field of vision for the user's eyes. Such conventional goggles have further comprised an elongated, elastomeric strap attached at either end thereof to corresponding ends of the anterior body for the purpose of holding the goggles on the head, or helmet, of the user by stretching the strap around the back of the head, or helmet, with the goggle positioned in opposing fashion on the face of the user. It has generally been accepted and understood among goggle wearers that different colors of lenses have been advantageous for different lighting and weather conditions.

The Need for Easily Interchangeable Lenses in Goggles

Earlier conventional goggles have not provided for interchangeable lenses. Not only has this resulted in a much less useful goggle as changing lighting conditions through the day have rendered a current goggle unsuitable for more easily distinguishing variations in terrain, especially snowy terrain of mostly a single color often having only slight shadows on the surface thereof to determine the presence of variations, but where the lens of the goggle has become damaged, or broken, such goggles have required replacement of the entire goggle.

More recently, conventional goggles have allowed for replacement of a damaged or broken lens, or replacement of a lens that is no longer suitable for changed lighting conditions. In such goggles, the body has comprised a flexible, but resilient, molded material forming a relatively deep vertically-oriented groove, often together with a plurality of notches on the lens matched with pegs in the groove for alignment and retention purposes. The notches and matched pegs have been designed to receive and hold the peripheral edge of the lens in a vertically-oriented fashion in the groove and to retain the lens in proper orientation on the pegs relative to the body.

When a user has desired to remove such a lens, they have pulled the flexible body members apart, disconnecting the notches and otherwise disassociating the lens from the groove in the body. Replacement with a different color lens has involved a reverse process of aligning the edge of the lens, and its notches, with their associated groove and pegs, first fitting an upper, or alternatively lower, portion of the lens into its associated groove and pegs, and then fitting the opposite portion of the lens into its associated groove and pegs. This process has been time-consuming and cumbersome, making it difficult for a user to easily interchange lenses, so much so that many have determined to not make an attempt to change the lens in the open, but rather to use a lens that has provided multi-purpose, though not ideal, use for most lighting conditions. Alternatively, where users have shown the patience necessary to have repeatedly changed lenses, these goggle bodies have lost some resiliency, broken, or cracked, due to repeated stressing of the bodies, and this has led to a lack of a engagement between the lens and the body.

Responsive to the difficulties of interchanging lenses for these types of goggles, there have been developed goggles having articulated frames designed for opening and closing to allow easier changing to lenses adapted for changed conditions. An example of such a frame is provided by U.S. Pat. No. 5,815,235, to Runckel, for Ski Goggles With Pivotal Frame Members For Interchanging Lenses. Similarly, published US Patent Application No. US20110225709A1, to Saylor et al., for Eyewear With Interchangeable Lens Mechanism, has facilitated the interchanging of lenses of such goggles with a biased outrigger, gate or latch for securing the lens relative to the goggle, the lens being further held in a proper orientation by one or more engagement members aligned with an aperture, or apertures, in the lens.

The Need for Anti-Fog Means in Goggles

Goggles are known to have become obscured with moisture when temperature and relative humidity conditions inside of the space defined between the goggle body and the user's face and eyes have been such that a dew point has been reached and condensation has formed like a "fog" on the inner surface of the goggle. This typically has happened when a colder inner surface of the goggle lens has come in contact with a now warmer and more humid area enclosed within the goggle body. There are many possible conditions which may lead to fogging of a goggle, since the dew point of the inside of the lens is affected by varying temperature, moisture, pressure and ventilation conditions. One common example of fogging has occurred when a person who has been skiing, cycling, hiking or engaging in other strenuous activity, stops moving as quickly as before, reducing the amount of air flow over the surfaces of the goggle, such that temperature differentials between the inner surface of the goggle and the now warmed and moist air within the goggle caused by the physical exertion and the enclosed space of the goggle have caused fogging.

Another example of fogging involves a significant increase in activity, increasing the amount of moisture and heat trapped within the goggle, primarily from perspiration and also from a higher incidence of exhaling moist warm air that is associated with such physical exertion. In such a case there has existed a greater imbalance in temperature between the inner surface of the goggle lens and the warm, moist air now trapped within the goggle, causing condensation and resulting fogging of the inner surface of the goggle lens.

Thus, fogging is a very common problem with goggles and this has occurred in various situations involving temperature extremes, and particularly warmer temperatures caused by perspiration and respiration entering within the goggle enclosure and which are warmer relative to colder temperature conditions outside of the goggle body. Of course this problem has ranged from being annoying to the user, to presenting a very dangerous situation where the user's field of vision has been greatly diminished while the user has been traveling at high speeds among fixed obstacles, such as trees, widely varying terrain such as bumps, cliffs, or other participants, or the user has otherwise been unable to clearly see an intended target or an enemy combatant. The problem of fogged goggles has resulted in injury and even death among goggle users.

Responsive to this common, annoying and even dangerous condition, great attention has been paid to solutions to the problem of fogging of goggles. For instance, numerous efforts have been made to increase the amount of passive airflow into the goggle. Examples of such may be found in US Patent Application Serial No. 20050193478 to Hussey, for Goggle Attachment System, and U.S. Pat. No. 6,665,885 to Masumoto, for Goggles.

Despite best efforts to produce a goggle that utilizes passive air-flow means for defogging the lens of the goggle, there are often present conditions which have rendered passive air-flow means of de-fogging ineffective. Such conditions have overwhelmed the ability of the passive means to overcome the temperature and humidity differentials presented by exertion by a user in cold, icing conditions or accumulation of snow clogging ventilation means. Also, sometimes a user's clothing, especially such as scarves or face masks, have impeded intended airflow of such goggles, rendering them ineffective.

As a result, there have even been developed goggles with active, personal fans to ventilate the enclosed space within and the inner surface of the lens of the goggle to mitigate the conditions leading to fogging. An example of such a system has been provided in U.S. Pat. No. 5,452,480, to Ryden, for Ski Goggles. One problem of such a device is that it does not necessarily overcome icing, snow accumulation or other blockage of outer goggle vents, thus rendering such a system less effective.

Regardless of the exact causes of fogging of a goggle in a particular situation, it has become understood that sufficient heating of the inner surface of the lens of the goggle comprises an effective means of removing fog from the lens and preventing further fogging. Accordingly, there have been developed various means of actively heating the inner surface of the goggle lens. One such means has comprised the placement of wires, or a resistive film surface, on the inner surface of the goggle lens, which wires or resistive surface have been attached to an electrical power source such as a DC battery carried on the goggle headband or jacket of the user in order to provide sufficient power to heat the lens. Examples of such a method of heating the lens of the goggle have been disclosed in U.S. Pat. No. 4,868,929, to Curcio, for Electrically Heated Ski Goggles, U.S. Pat. No. 5,459,533, to McCooeye et al., for Defogging Eye Wear, and Published US Patent Application Serial No. US20090151057, to Lebel et al., for Reversible Strap-Mounting Clips for Goggles.

Thus, while there have been devised independent solutions to a need for easily interchanging the lens on a sport or standard-issue military goggle and the need for maintaining such a goggle fog free, there yet exists a need for a sport or standard-issue military goggle that provides not only an easily interchangeable lens system, but also provides an active, effective means of heating the lens to prevent fogging. In particular, there exists a need for an efficient and effective means of both releasably attaching the lens of a goggle to its body and therefore preferably allowing for efficient, simultaneous interconnection of the lens to a source for heating of the lens when necessary to prevent fogging. Ideally, such a system would be easy to operate, even with a gloved hand, and would be provided in a goggle that is relatively inexpensive to manufacture, and is thus affordable, for sporting and standard issue military ground operation applications.

SUMMARY OF THE INVENTION

In accordance with a first aspect of the invention, there is provided an anti-fog, interchangeable-lens goggle adapted for use with a battery comprising: a body, an anti-fog lens, a lens/body engagement means or mechanism, electrical interconnection and lens/body attachment reinforcing means or mechanism operable with the lens/body engagement mechanism, and strap means for holding the goggle on the user's head or helmet.

The body comprises first and second ends, a flexible posterior portion adapted for engaging a user's face adjacent the user's eyes, and a semi-rigid anterior portion.

The lens comprises an anti-fog heating element thereon and is adapted for engaging the semi-rigid anterior portion of the body a distance from the user's eyes so as to provide a shield to the eyes.

The engagement mechanism comprises a portion thereof attached to the lens and a portion thereof attached to the body, for releasably interconnecting the lens and the semi-rigid anterior portion of the body. Preferably, the engagement mechanism further comprises tongue-and-groove members, or a tongue-and-groove seal, wherein one of the tongue-and-groove is on a periphery of the lens and the other of the tongue-and-groove is on a periphery of the anterior portion of the body. Alternatively, the engagement mechanism may further comprise cap-and-ridge members, or a cap-and-ridge seal, wherein the cap is on a periphery of the lens and the ridge is on a periphery of the anterior portion of the body.

The interconnecting means depends from the body and is adapted for detachably interconnecting the heating element of the lens and the battery. Further, the interconnecting means is operable with the engagement mechanism such that interconnecting the heating element of the lens with the battery also reinforces interconnecting of the lens with the semi-rigid anterior portion of the body, and such that disconnecting the heating element and the battery also releases the lens for disengagement from the semi-rigid anterior portion of the body.

The interconnecting means adapted for detachably interconnecting the heating element of the lens and the battery further comprises a hook on the lens and a latch pivotably mounted to the body for engagement with the hook of the lens. Such a latch is preferably operable to a first position to bias an end of the lens against the body, thus reinforcing attachment of the lens on the body, and to interconnect the heating element of the lens and the battery, the latch preferably also being operable to a second position to release the lens for removal from the semi-rigid anterior portion of the body and to disconnect the heating element of the lens from the battery.

Alternatively, the interconnecting means adapted for detachably interconnecting the heating element of the lens and the battery may further comprise a pivotably latching gate on the body, the gate being operable to a first position to bias an end of the lens against the body. Thus, the gate reinforces attachment of the lens on the body and interconnects the heating element of the lens with the battery. The gate is also operable to a second position to release the lens for removal from the body and to disconnect the heating element of the lens from the battery.

Still further, in an alternative embodiment, the interconnecting means adapted for detachably interconnecting the heating element of the lens and the battery may further comprise a stretchy silicone band around the lens and a post on each end of the goggle frame, or at intermediate locations around the goggle frame, the silicone band forming a plurality of stretchy bands, or loops, one band at each end of the lens, or at intermediate locations around the lens, and adapted to be operable to a first position for looping or wrapping around corresponding posts at the ends of the body, or at intermediate locations around the body, to bias the lens against the body, thus reinforcing attachment of the lens on the body, and to interconnect the heating element of the lens and the battery, each stretchy band operable to a second position disconnected from the corresponding post to release the lens for removal from the body and to disconnect the heating element of the lens from the battery.

In this embodiment, contacts for interconnecting the heating element on the lens and the battery may reside on the lens and frame of the goggle, or alternatively on the silicone band and the frame of the goggle or the posts at either end of the goggle. In this embodiment, the post may carry buttons for control of the electronics, wherein the buttons may or may not be covered with silicone.

Further still, in an alternative embodiment, the interconnecting means adapted for detachably interconnecting the heating element of the lens and the battery may further comprise an outer peripheral member, such as a silicone skin, or anterior plastic face or frame, having one or more interconnection members, such as nub-like silicone engagement members, or alternatively more rigid clip members depending from the anterior plastic face or frame, adapted for residing in corresponding receptacles defined around an outer periphery on the goggle body made of a more rigid material, such as plastic, each receptacle adapted for receiving and retaining a corresponding interconnection or clip member in a first closed position to bias the lens on the goggle body, thus reinforcing attachment of the lens on the body, and to interconnect the heating element of the lens and the battery, the interconnection members being operable to an open position disconnected from the corresponding receptacles to disconnect the heating element of the lens from the battery. In this embodiment, the lens either resides between the goggle frame and the outer silicone skin, or anterior face or frame, the lens being held in place on the goggle frame by the outer silicone skin, or anterior face or frame. In this embodiment, contacts for interconnecting the heating element on the lens and the battery may reside on the lens and body of the goggle.

In another alternative embodiment, the interconnecting means adapted for detachably interconnecting the heating element of the lens and the battery may further comprise a pop-off anterior face having a plurality of clip-like, or hook-like, engagement members adapted for positive receipt and engagement in snap receptacles on the more rigid goggle plastic body. In this embodiment, the lens may reside between the pop-off anterior face and the goggle body, as in the case of the silicone anterior face described above, or the lens may be part of the more rigid pop-off anterior face. In this embodiment, contacts for interconnecting the heating element on the lens and the battery may reside on the lens and body of the goggle.

The strap means comprises first and second ends, the first end of the strap means being interconnected with the first end of the body, and the second end of the strap means being interconnected with the second end of the body, so as to be adapted for holding the goggle on the user's head or helmet. The strap may comprise a traditional strap, or it may comprise a silicone strap that is especially adapted for engagement with a helmet. The battery may be carried in a water-proof case and carried on or in the strap, in the body of the goggle, or in the user's clothing.

This aspect of the invention addresses and alleviates problems presented by conventional goggles in that it provides for an easily interchangeable lens in a goggle that is also adapted for fog-free wearing pleasure. Thus, users are enabled in interchanging one fog-free lens with another fog-free lens to adapt to varying lighting and weather conditions without enduring the hassle associated with conventional goggles to successfully get the lens back in the frame. Further, users are enabled in interchanging a non-fog-free lens with a fog-free lens, as both types of lenses are interchangeable with the present invention. By minimizing the number of steps a user must take to interchange lenses, as well as to use the fog-free characteristics of the present invention, users will be more apt to use and benefit from the features of the improved goggle.

In accordance with another aspect of the invention, there is provided an anti-fog, interchangeable-lens goggle adapted for use with a battery comprising: a body, an anti-fog lens, engagement mechanism for both interconnecting the lens to the body and the lens to the battery, and strap means for holding the goggle on a user's head.

The body, lens and strap portions of this aspect of the invention are like the body, lens and strap portions in accordance with the aspect of the invention described above, and it will be apparent that various types of electrically heated lenses, such as resistive element coating-type lenses, embedded wire-type lenses, resistive element lenses, etc., may be adapted for use with the goggle of the invention without departing from the true scope and spirit of the invention as set forth in the claims appended hereto.

The engagement mechanism is adapted for interconnecting the anti-fog heating element of the lens with the battery, a part of the engagement mechanism being connected to the body and a part of the engagement mechanism being connected to the lens. The engagement mechanism is preferably operable between first engaged and second disengaged positions, wherein operation of the engagement mechanism to the first engaged position releasably interconnects the lens with the semi-rigid anterior portion of the body and releasably interconnects the anti-fog heating element of the lens with the battery. Operating of the engagement mechanism to the second disengaged position removes the lens from the semi-rigid anterior portion of the body and disconnects the anti-fog heating element of the lens from the power source.

The interconnection mechanism of the goggle in accordance with this aspect of the invention further comprises tongue-and-groove members wherein one of the tongue-and-groove is on a periphery of the lens and the other of the tongue-and-groove is on a periphery of the anterior portion of the body. Alternatively, the interconnection mechanism further comprises cap-and-ridge members wherein the cap is on a periphery of the lens and the ridge is on a periphery of the anterior portion of the body.

This aspect of the invention further simplifies the interchanging of a lens on a goggle that is adaptable to anti-fogging incorporated into or onto the lens in that only a single step, essentially peeling one lens off the anterior periphery of the goggle, is required for the user to remove the lens, and a single step, essentially engaging the anterior periphery with the periphery of another lens, is required. Making of the electrical connection with the power source with this aspect of the invention is essentially simultaneous, or automated, with interchanging of the lens, without any additional steps being further necessary to make the connection for power to the lens. Of course, it may be advantageous to provide an on/off switch (in actuality typically a high/low power switch) on the battery power system to allow conservation of battery power when not in use, but operation of such is not seen as an additional step to interchanging of lenses, since such interchanging may be accomplished with no risk to the user or the system in low-voltage power systems without first switching off the battery.

The anti-fog, interchangeable-lens goggle of this aspect of the invention may further comprise an interconnection mechanism, a part of the interconnection mechanism being connected to the body and a part of the interconnection mechanism being connected to the lens. The interconnection mechanism in accordance with this aspect of the invention is for reinforcing engagement of the lens and the semi-rigid anterior portion of the body. The interconnection mechanism may comprise a plurality of hooks, at least one hook depending from the first end of the lens, at least one hook depending from the second end of the lens, the interconnection mechanism further comprising a plurality of latches, at least one latch being pivotably attached to the first end of the body, at least one latch being pivotably attached to the second end of the body. Each latch engages with one of the hooks to releasably interconnect the lens with the semi-rigid anterior portion of the body and to releasably interconnect the anti-fog heating element of the lens with the battery in the first engaged position of each latch. In a second, disengaged, position of each latch, the lens is released from the semi-rigid anterior portion of the body, and the anti-fog heating element of the lens is disconnected from the battery.

The interconnection mechanism of this aspect of the invention may alternatively comprise a plurality of latching gates, at least one gate being pivotably attached to the first end of the body, at least one gate being pivotably attached to the second end of the body. Each such gate is operable to a first position to bias an end of the lens against the body, thus reinforcing attachment of the lens on the body, each gate also interconnecting the heating element of the lens and the battery. Each such gate is also operable to a second position to release the lens for removal from the body and to disconnect the heating element of the lens from the battery.

Further, in accordance with this aspect of the invention, the interconnection mechanism may alternatively comprise a silicone band and post combination, an outer silicone skin or peripheral member, or a pop-off face with clip-type interconnections, all as mentioned previously in connection with a previous aspect of the invention.

In accordance with another aspect of the invention, there is provided a goggle with an easily interchangeable lens adapted for accommodating various weather, lighting and fogging conditions comprising: a body, a lens, a peel-off horizontal tongue-and-groove engagement mechanism for releasably interconnecting the lens and the body, and a strap means.

The body, lens and strap of this aspect of the invention is like the body, lens and strap of other aspects of the invention described above. The peel-off horizontal tongue-and-groove engagement mechanism comprises one of the tongue-and-groove being attached around the periphery of the lens, the other of the tongue-and-groove being attached around the periphery of the semi-rigid anterior portion of the body, for releasably interconnecting the lens and the semi-rigid anterior portion of the body. Alternatively, the goggle in accordance with this aspect of the invention may comprise a peel-off cap-and-ridge engagement mechanism, the cap being attached around the periphery of the lens, the ridge being attached around the periphery of the semi-rigid anterior portion of the body, for releasably interconnecting the lens and the semi-rigid anterior portion of the body.

The goggle provided in accordance with this aspect of the invention is suitable for use with or without a heated lens, it being the case that the user may have at ready whichever type of goggle lens the user needs given weather, lighting and fogging conditions, such as relative humidity inside and outside of the goggle, outside temperature, body temperature, difficulty of terrain leading to greater exertion, and barometric pressure conditions. Users of goggles rarely can anticipate with certainty what such conditions will be on any given day, so it is important to have a goggle that is widely adaptable to the many and varied conditions that may be encountered on any given day.

The goggle in accordance with this aspect of the invention, regardless of whether a tongue-and-groove or cap-and-ridge engagement mechanism is employed, may further comprise interconnection mechanism, such as a latch depending from the body and operable between open and closed positions such that in the closed position the latch biases the lens onto the semi-rigid anterior portion of the body and thus reinforces the releasable interconnection of the lens and the semi-rigid anterior portion of the body, and in the open position of the latch the lens is released for removal from the semi-rigid anterior portion of the body.

Further, in accordance with this aspect of the invention, the interconnection mechanism may alternatively comprise a silicone band and post combination, an outer silicone skin or face, or a pop-off face with clip-type interconnections, all as mentioned previously in connection with the first aspect of the invention.

Moreover, the lens of the goggle in accordance with this aspect of the invention, again regardless of whether a tongue-and-groove or cap-and-ridge engagement mechanism is employed, or regardless of whether a latch, a silicone band-and-post combination, an outer silicone skin or face, or a pop-off face is employed, may further comprise an anti-fog heating element on the lens and adapted for connection with a battery. In such case, interconnection of the lens to the body also connects the anti-fog heating element on the lens with the battery.

Thus, the goggle in accordance with this aspect of the invention is readily adapted for use with fully interchangeable lenses, whether they be lenses for a sunny day with, or without, anti-fog means incorporated, whether they be lenses for a cloudy day with, or without, anti-fog means incorporated, or whether they be lenses adapted for rain, or heavy snow, or some weather condition in-between. In such case the user will be encouraged to make appropriate lens changes, thus contributing to the safety of clearer vision through an appropriately chosen goggle by using the goggle of the invention, because interchanging of the lens and virtually automated interconnection of an electrical heat source to the goggle, when desirable, is assured.

In accordance with another embodiment of the invention, there is provided a goggle having an anti-fog, interchangeable-lens and adapted for use with a battery comprising: a semi-rigid peripheral body having first and second ends, an anterior portion and a posterior portion; a peripheral lens frame having a semi-flexible anterior portion adapted for engaging the semi-rigid posterior portion of the peripheral body, the lens frame having a flexible posterior portion adapted for engaging the user's face around the user's eyes; a lens mounted in the lens frame and having an electric heating element thereon, the lens and the lens frame defining a single goggle enclosure and so as to provide a shield to the eyes. This embodiment of the goggle further comprises an engagement mechanism, having a portion thereof attached to the lens frame and a portion thereof attached to the body, for releasably interconnecting the lens frame and the semi-flexible posterior portion of the body; interconnecting strap means depending from the body and adapted for detachably interconnecting the heating element of the lens and the battery, the interconnecting strap means operable with the engagement mechanism such that interconnecting the heating element of the lens with the battery also reinforces interconnecting of the lens with the semi-rigid anterior portion of the body, and such that disconnecting the heating element and the battery also releases the lens for disengagement from the semi-rigid posterior portion of the body, the strap means adapted for holding the goggle on one of a user's head and helmet. Preferably, the goggle body of this embodiment of the invention is adapted for holding the battery, and further, preferably, the body of this embodiment further comprises an on/off switch for the battery and a test button for signaling battery strength. Alternatively, the battery may be carried on a posterior body portion of the goggle while the lens and peripheral frame may be adapted to attach to an anterior portion of the body while the strap holds the body and frame together, thus reinforcing the interconnection between the battery and the heating element of the lens. These additional features of the invention render it even easier to operate the goggles in an anti-fog mode, since simply placing the goggles on the user's head would serve to reinforce the engagement of the easily interchangeable lens and the body of the goggle and would also serve to make an electrical connection between the heating element of the goggle and the battery power sources. With this embodiment of the invention, as with other embodiments and aspects of the invention, the battery may be carried on, or in, the strap, with wires passing through, or externally of, the strap to the body of the goggle, or lens frame, as the case may be.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

Figure 4A:
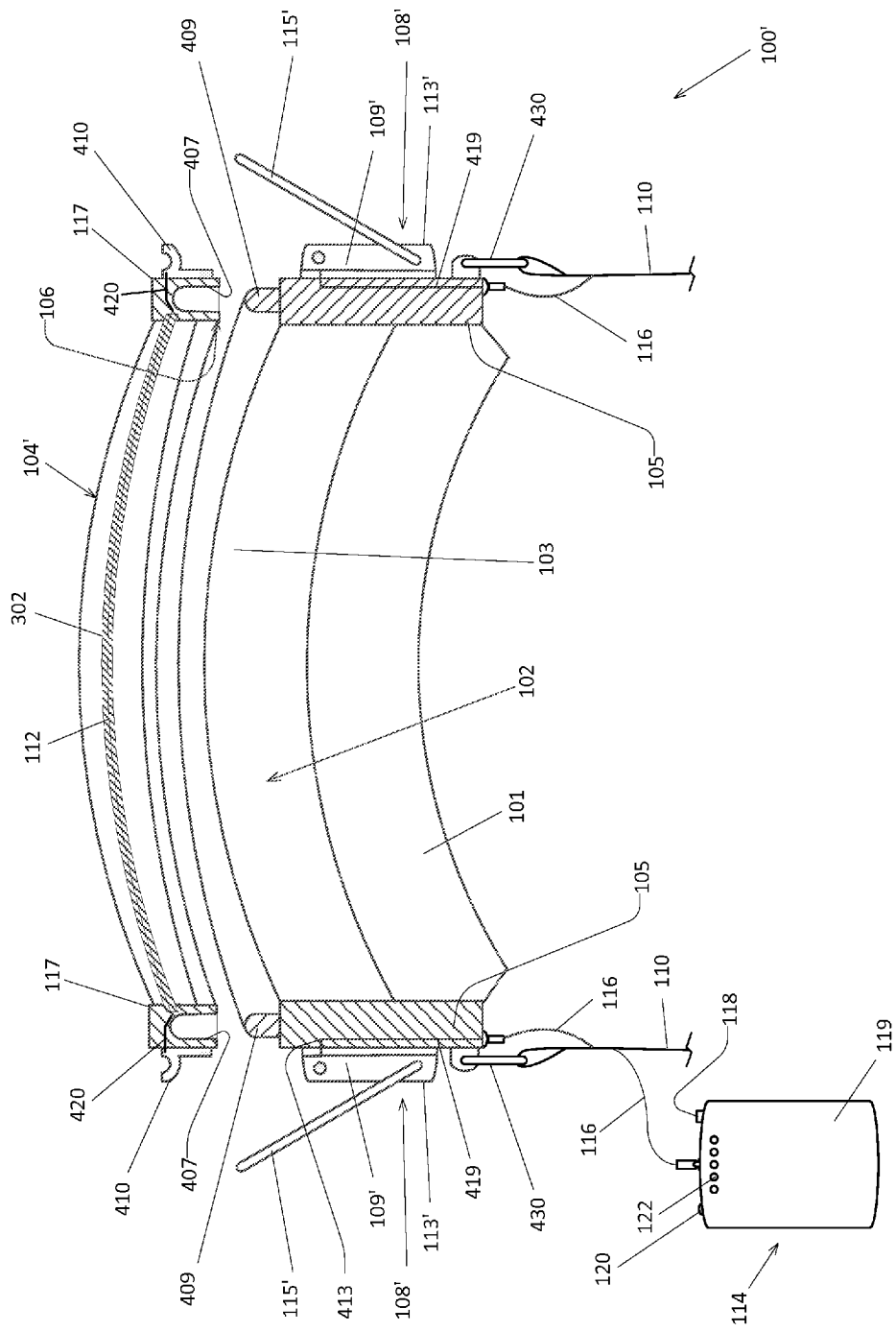
FIG. 4a is a top view of a tongue-and-groove engagement mechanism alternate embodiment of a goggle showing the detachable lens and goggle body portions thereof in cross-section as shown generally in FIG. 4k and prior to the detachable lens being installed on the goggle body.
Figure 4B:
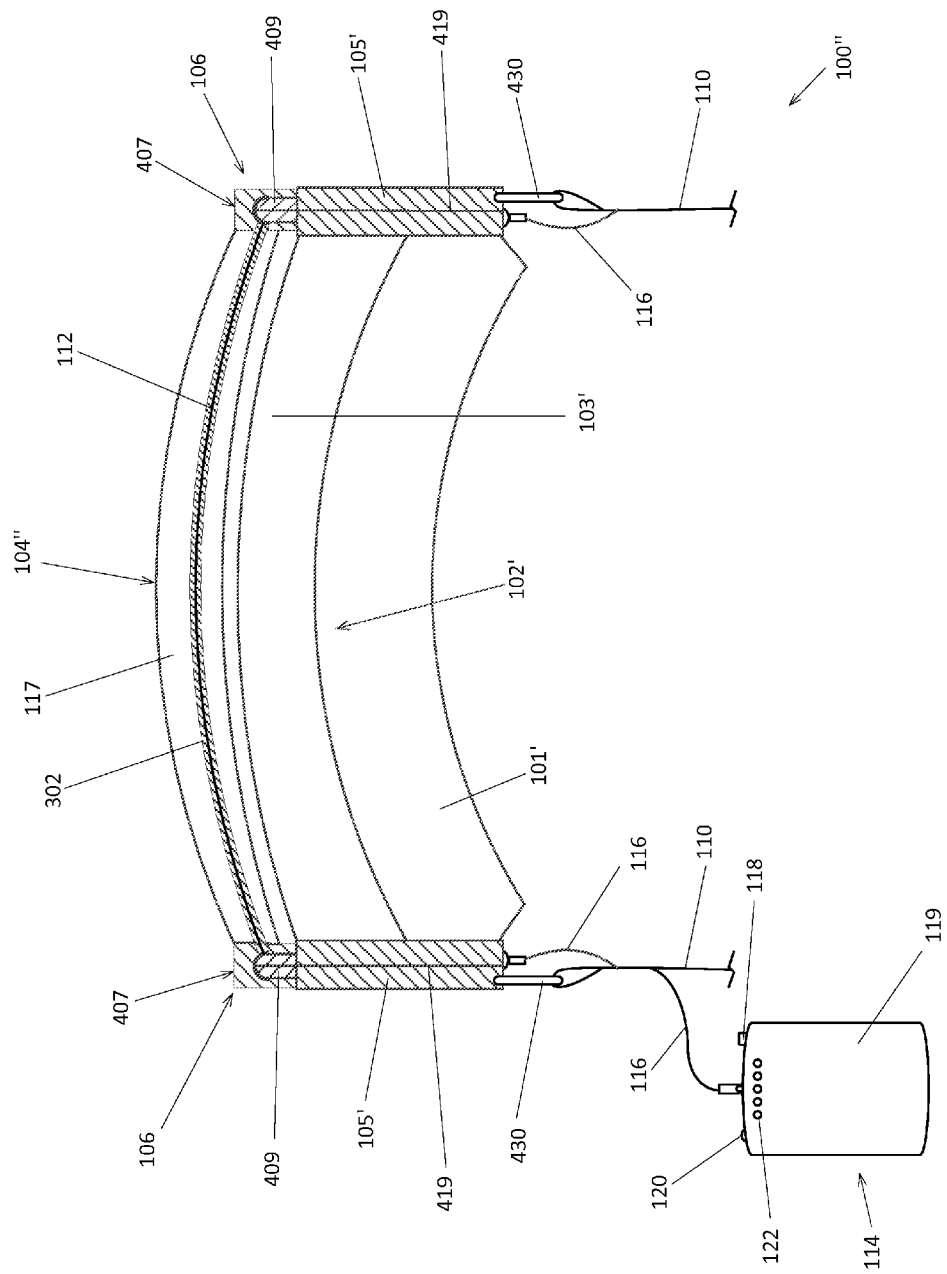
FIG. 4b is a top view of a tongue-and-groove engagement mechanism alternate embodiment of a goggle in accordance with the invention showing the lens and body of the goggle in cross-section as shown generally in FIG. 4k, not having a reinforcing latch or gate, and the lens having been installed on the goggle body.
Figure 4C:
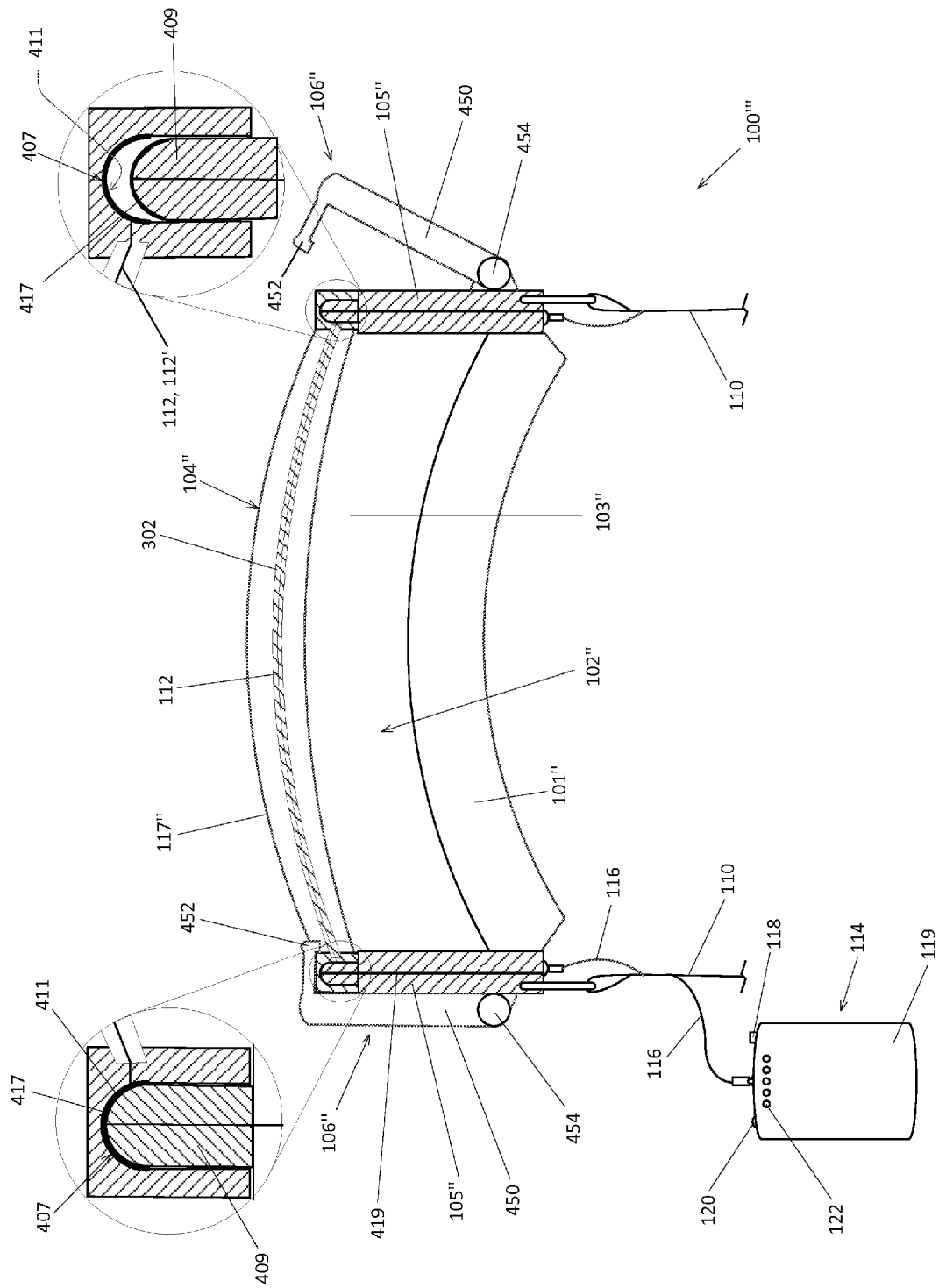
Figure 4D:
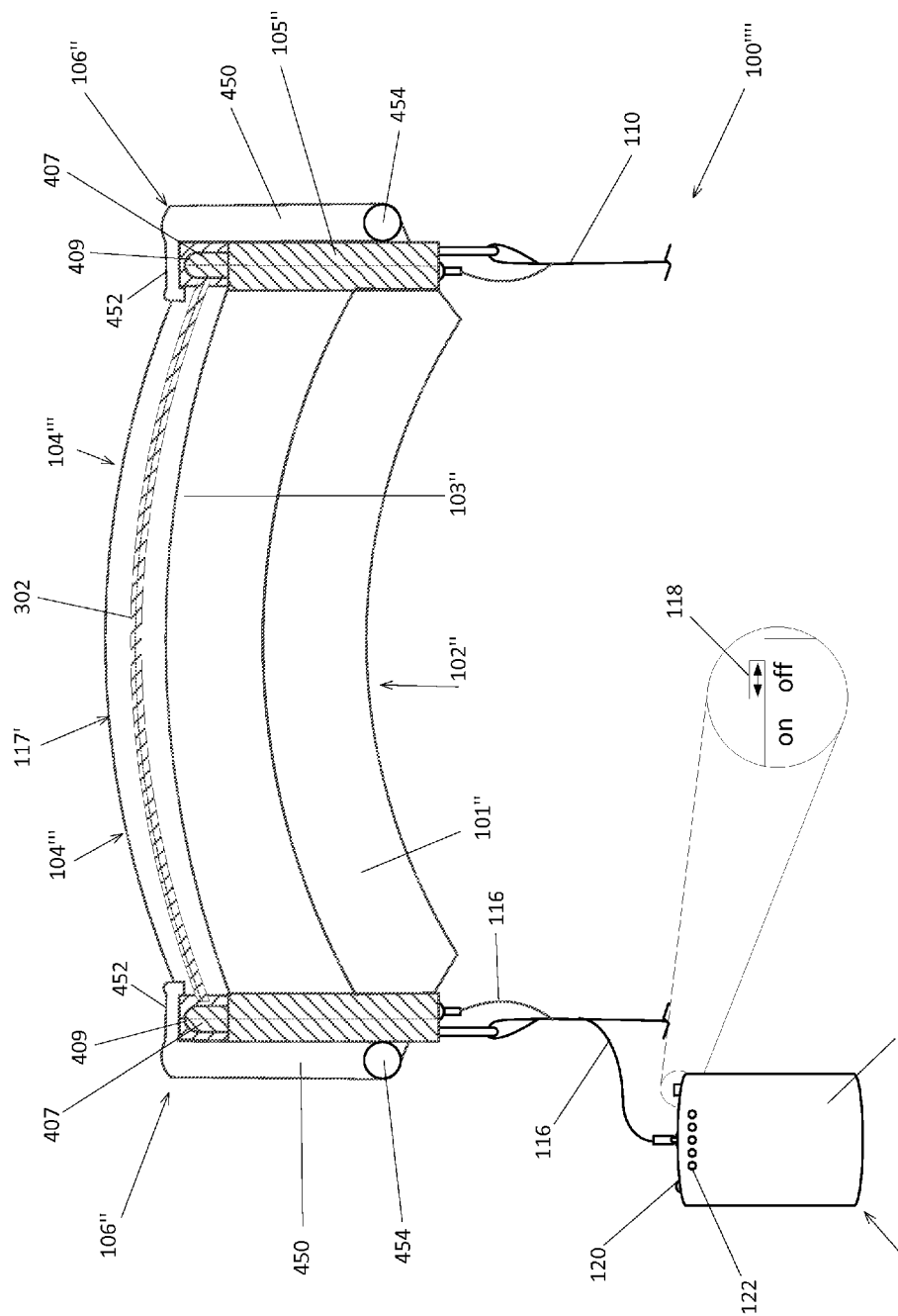
Figure 4E:
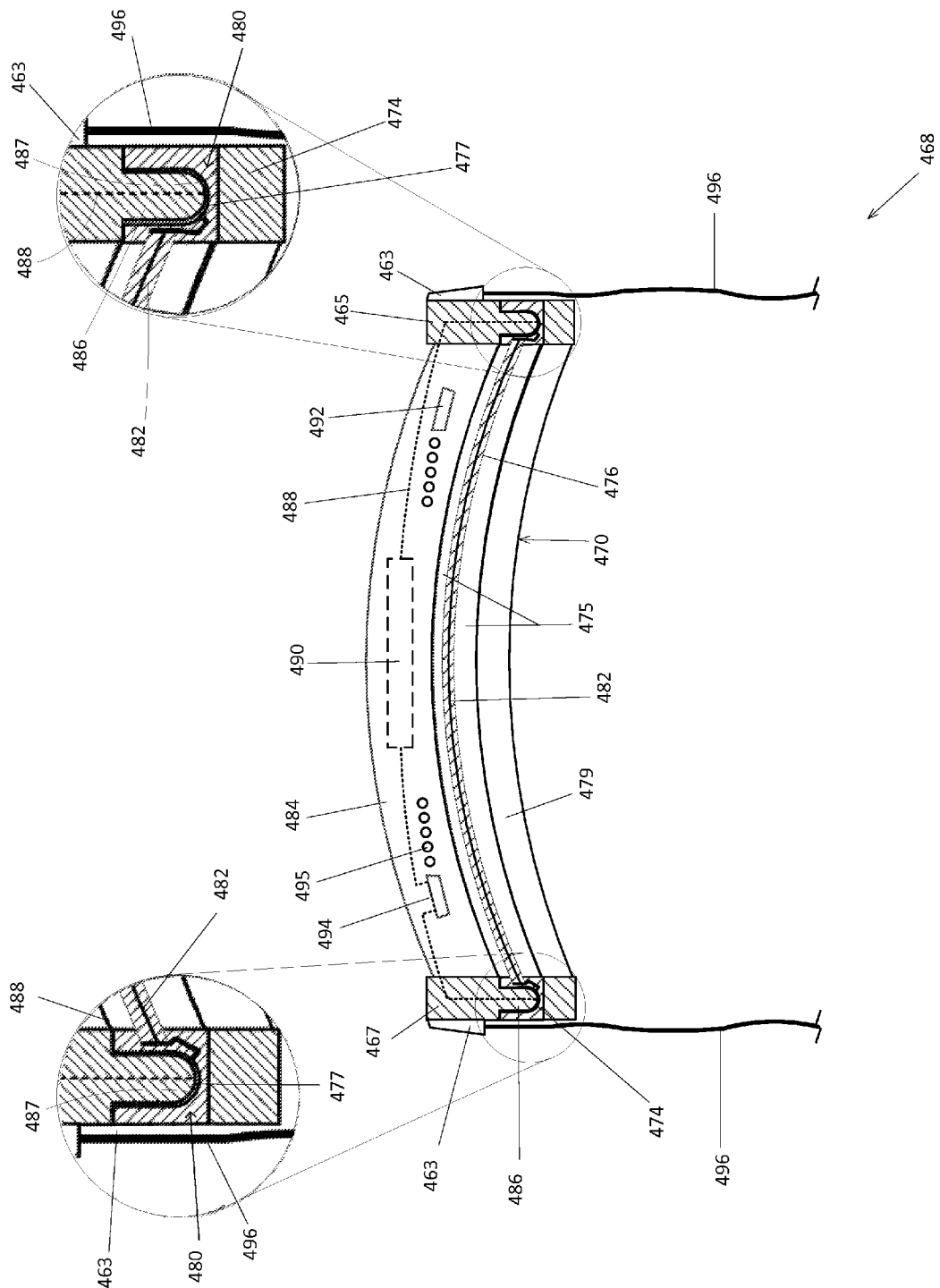
Figure 4F:
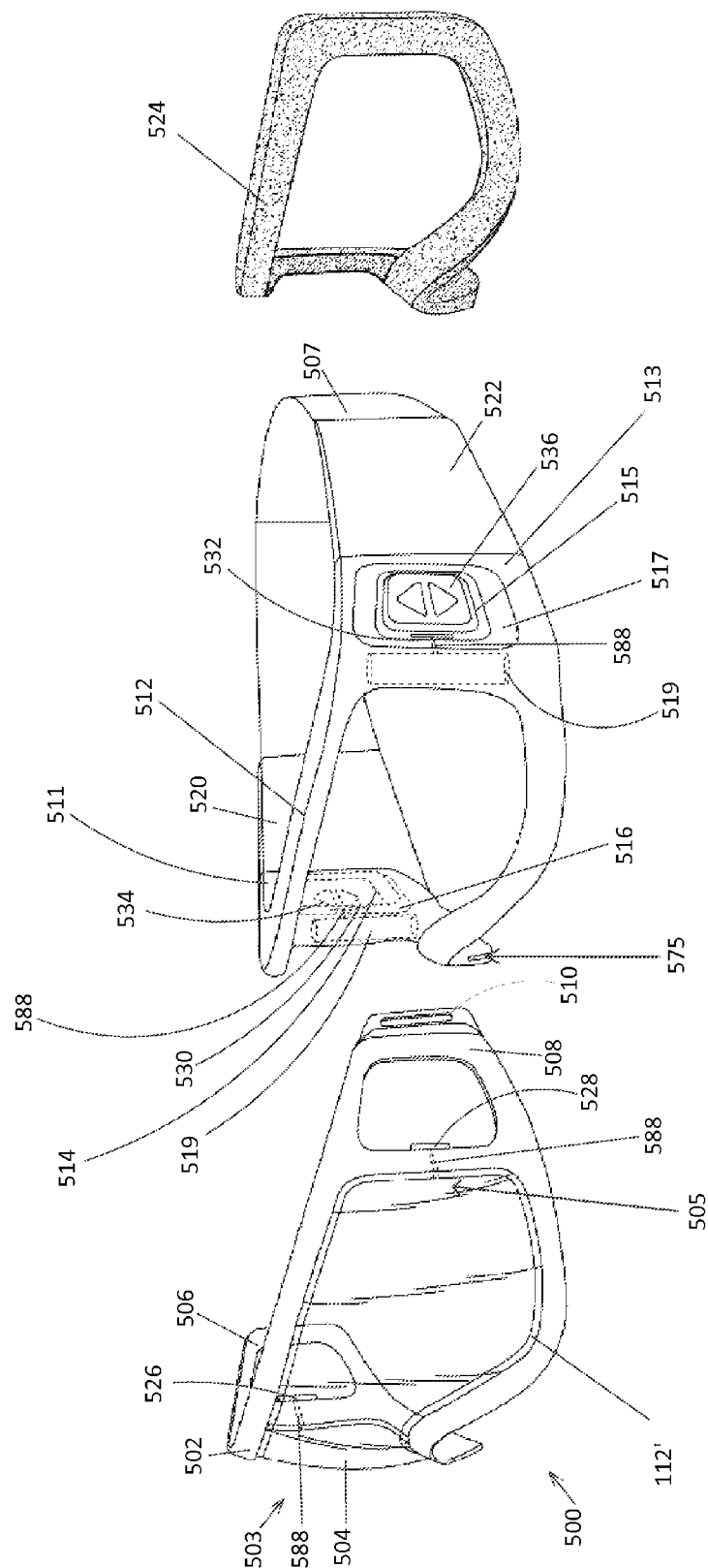
Figure 4G:
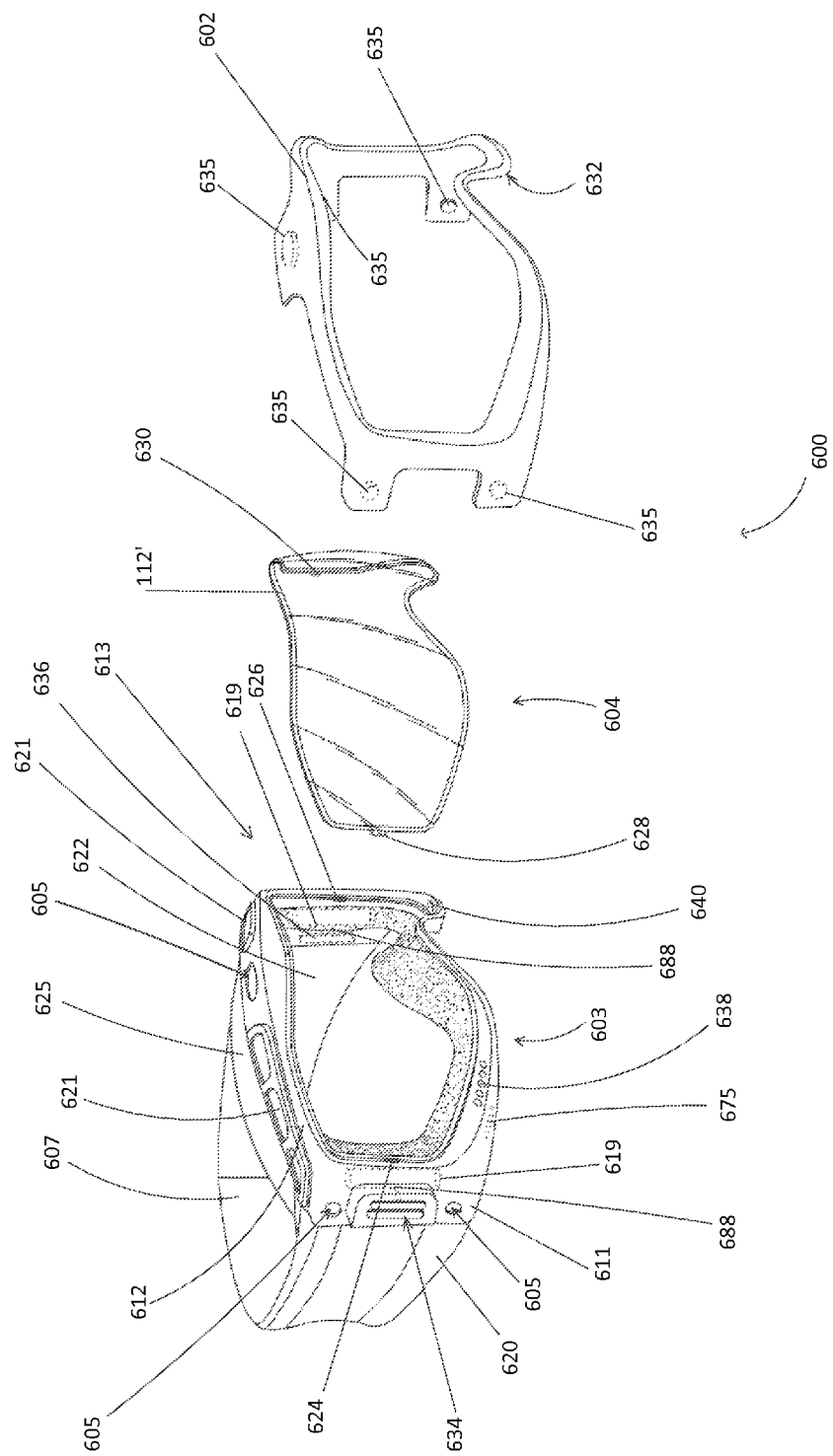
Figure 4H:
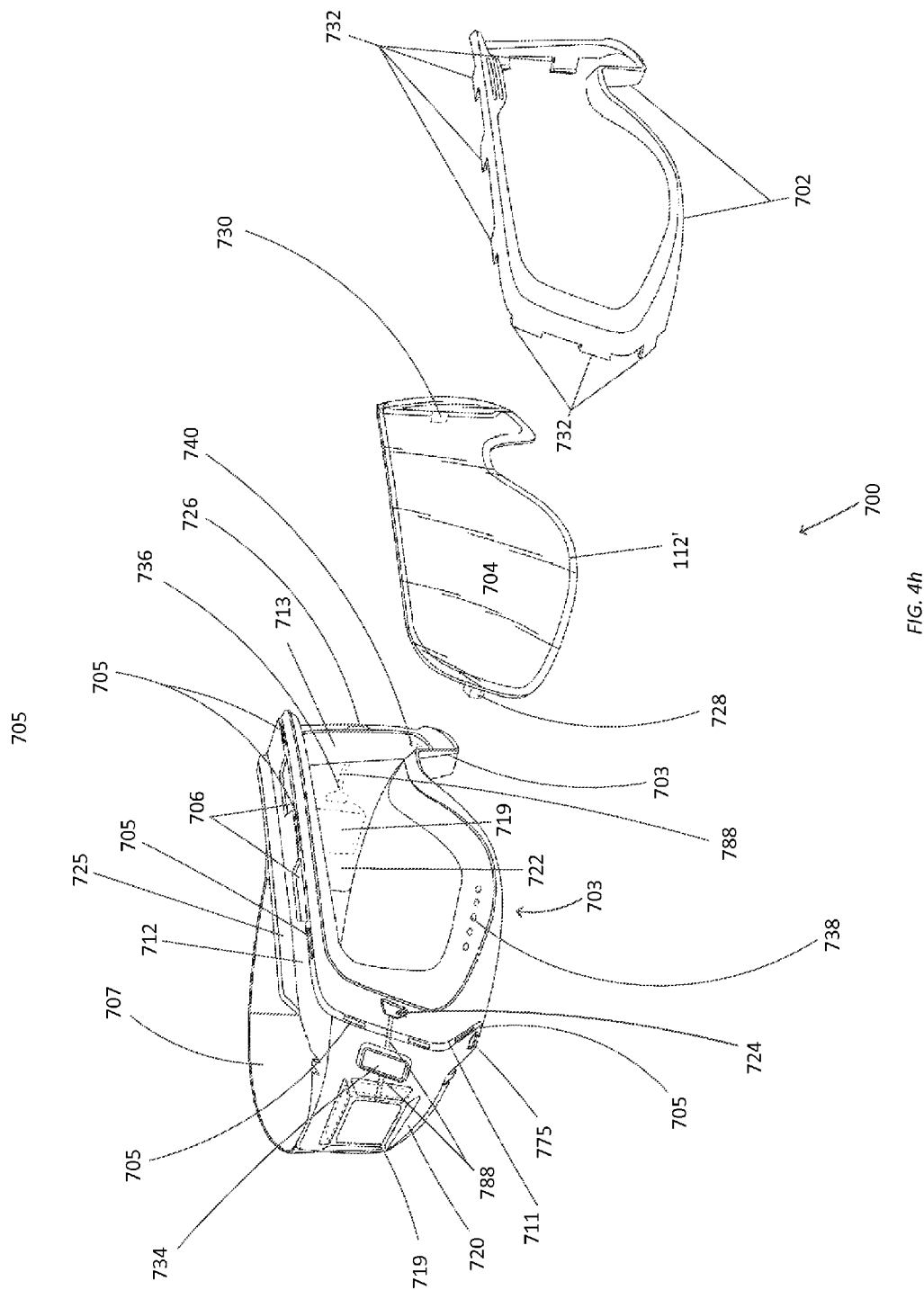
Figure 4I:
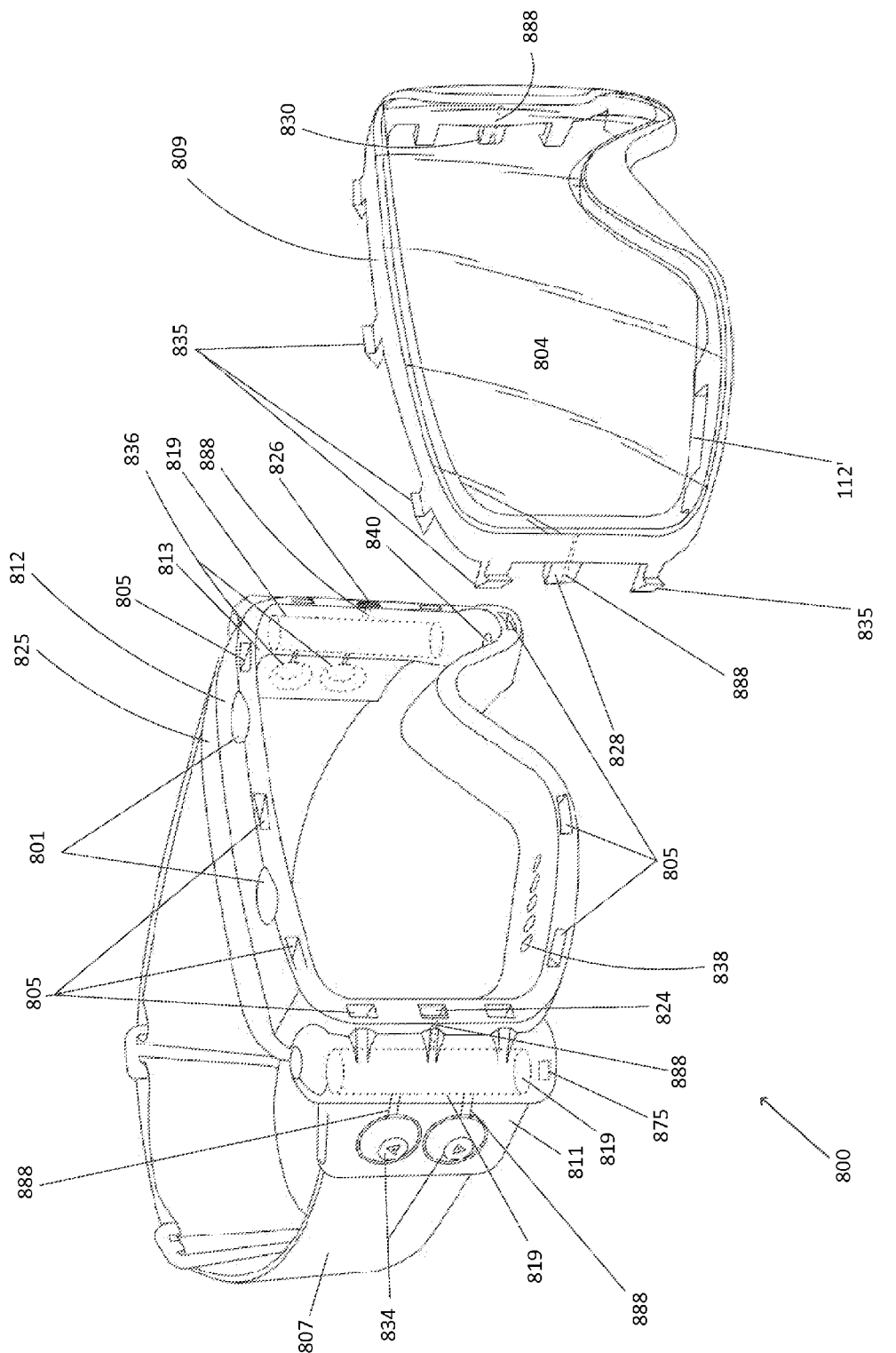
Figure 4J:
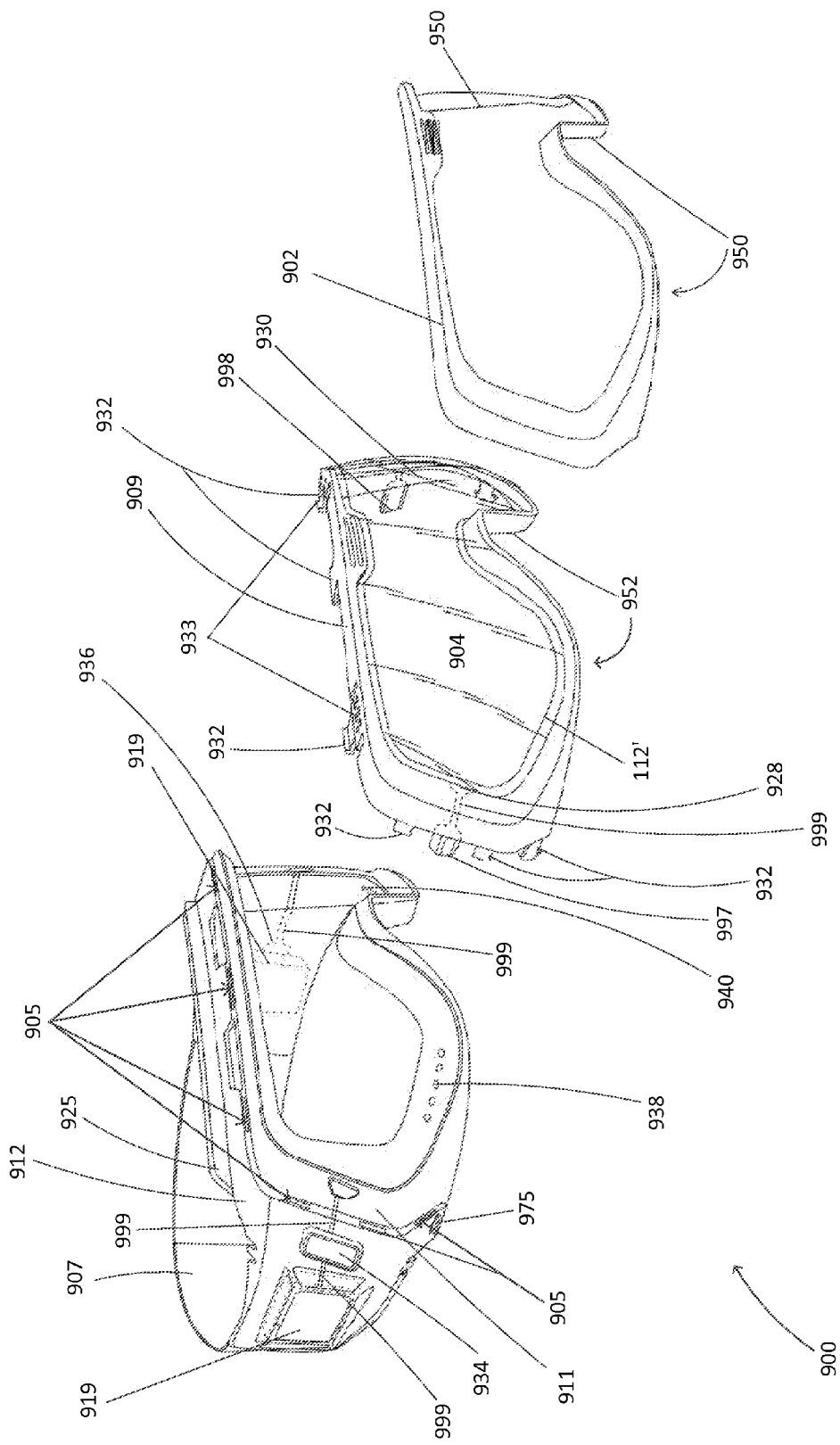
Figure 4K:
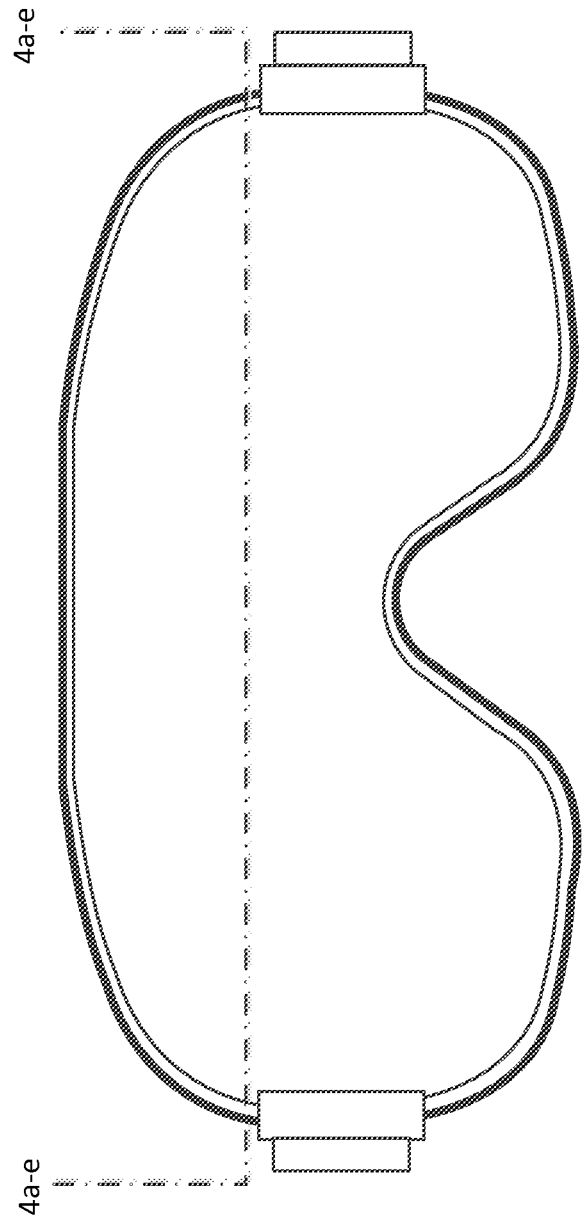
Figure 5C:
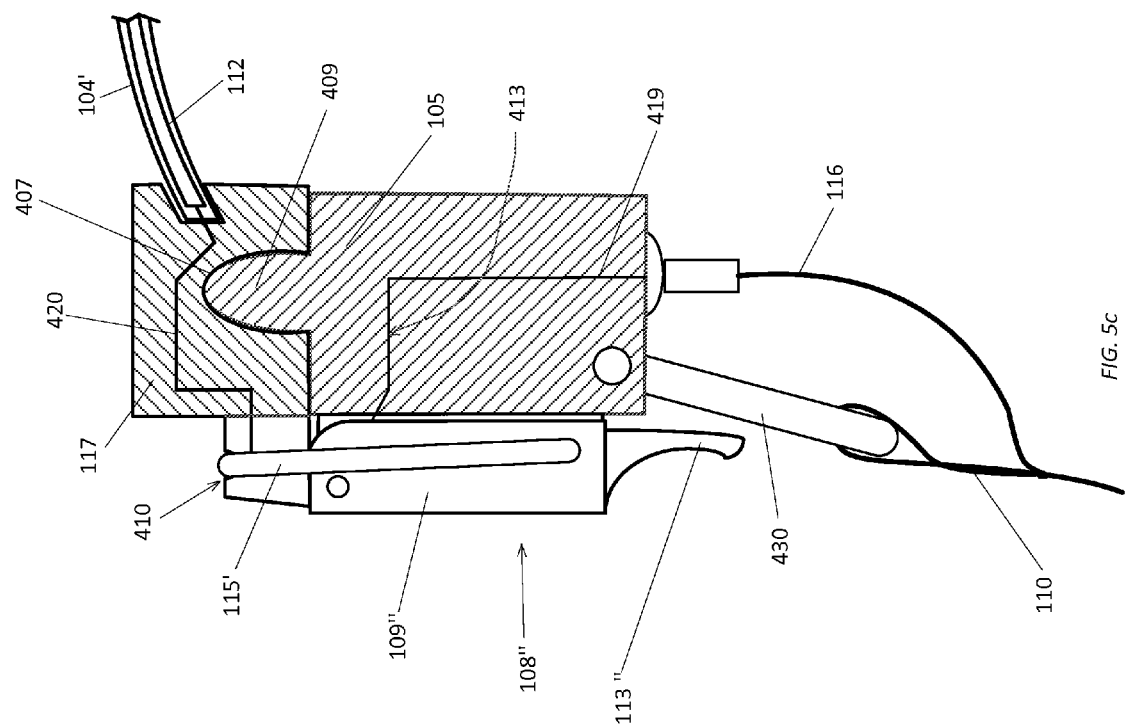
Figure 6:
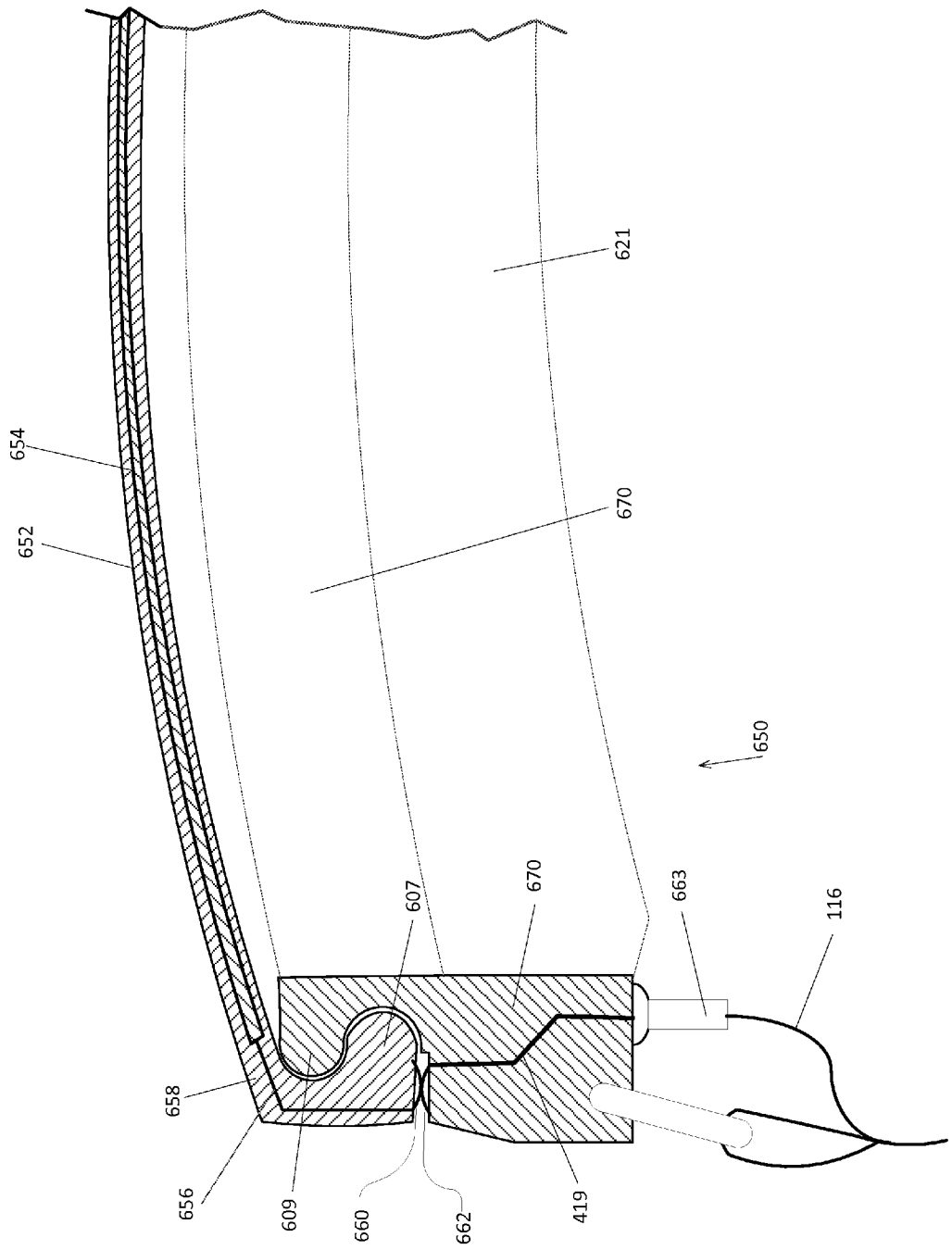
Figure 7:
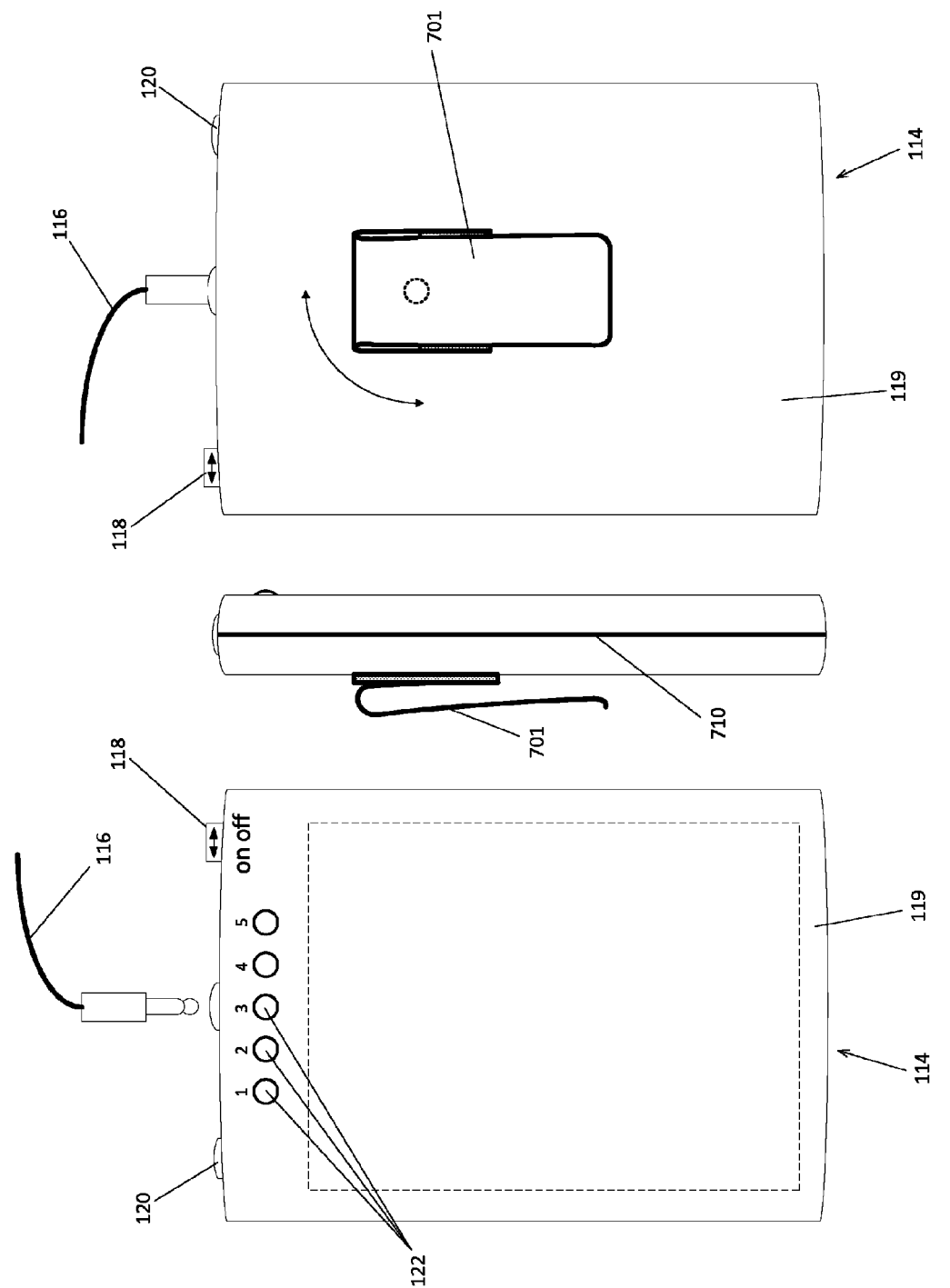

4c is a top view of another tongue-and-groove engagement mechanism alternate embodiment of a goggle in accordance with the invention showing an anti-fog goggle lens and body of the goggle in cross-section as shown generally in FIG. 4k, having a reinforcing gate, and having been partially installed on the goggle body;

FIG. 4d is a top view of the tongue-and-groove engagement mechanism alternate embodiment of FIG. 4c but showing a non-anti-fog goggle lens of the goggle in cross-section as shown generally in FIG. 4k, having a reinforcing gate, and having been installed on the goggle body;

FIG. 4e is a top view of a tongue-and-groove engagement mechanism alternate embodiment anti-fog goggle showing the lens of the goggle in the lens frame in cross section as shown generally in FIG. 4k, with the straps of the goggle on the goggle body such that wearing of the goggle biases a switch in the goggle to activate anti-fog circuitry within the goggle frame;

FIG. 4f is a perspective view of a silicone band and post interconnection mechanism for an alternate embodiment of an anti-fog goggle with the lens frame and goggle body portions of the goggle shown as exploded modular components;

FIG. 4g is a perspective view of a silicone skin or face interconnection mechanism for an alternate embodiment of an anti-fog goggle with the silicone skin or face, the lens and the goggle body portions of the goggle shown as exploded modular components;

FIG. 4h is a perspective view of a snap-on face interconnection mechanism for an alternate embodiment of an anti-fog goggle with the face, lens and goggle body portions of the goggle shown as exploded modular components;

FIG. 4i is a perspective view of a clip-on full lens face interconnection mechanism for an alternate embodiment of an anti-fog goggle with the lens face/frame and goggle body portions of the goggle shown as exploded modular components;

FIG. 4j is a perspective view of a clip-on lens interconnection mechanism for an alternate embodiment of an anti-fog goggle with the face, lens frame and goggle body portions of the goggle shown as exploded modular components;

FIG. 4k is a front view of a generic anti-fog goggle demonstrating the cross section cuts taken for FIGS. 4a-4e;

FIG. 5a is a detailed view showing part of the wiring and interconnection mechanism of an embodiment of the goggle of FIG. 4a, with the lens shown in cross-section and prior to installation on the body of the goggle;

FIG. 5b is a detailed view showing part of the wiring and interconnection mechanism of the embodiment of the goggle of FIG. 4a, with the lens shown in cross-section and partially installed on the body of the goggle;

FIG. 5c is a detailed view showing part of the wiring and interconnection mechanism of the embodiment of the goggle of FIG. 4a, with the lens shown in cross-section and installed on the body of the goggle;

FIG. 6 is a top section view showing yet another alternate embodiment engagement mechanism comprising a cap-and-ridge engagement mechanism for a goggle in accordance with the present invention; and FIG. 7 shows front, side and back views of an alternate water-proof battery pack suitable for primary or backup secondary power having a clip for attaching to a goggle strap, other equipment or other clothing and suitable for use with an anti-fog, interchangeable-lens goggle in accordance with the invention.

DETAILED DESCRIPTION

Figure 1:
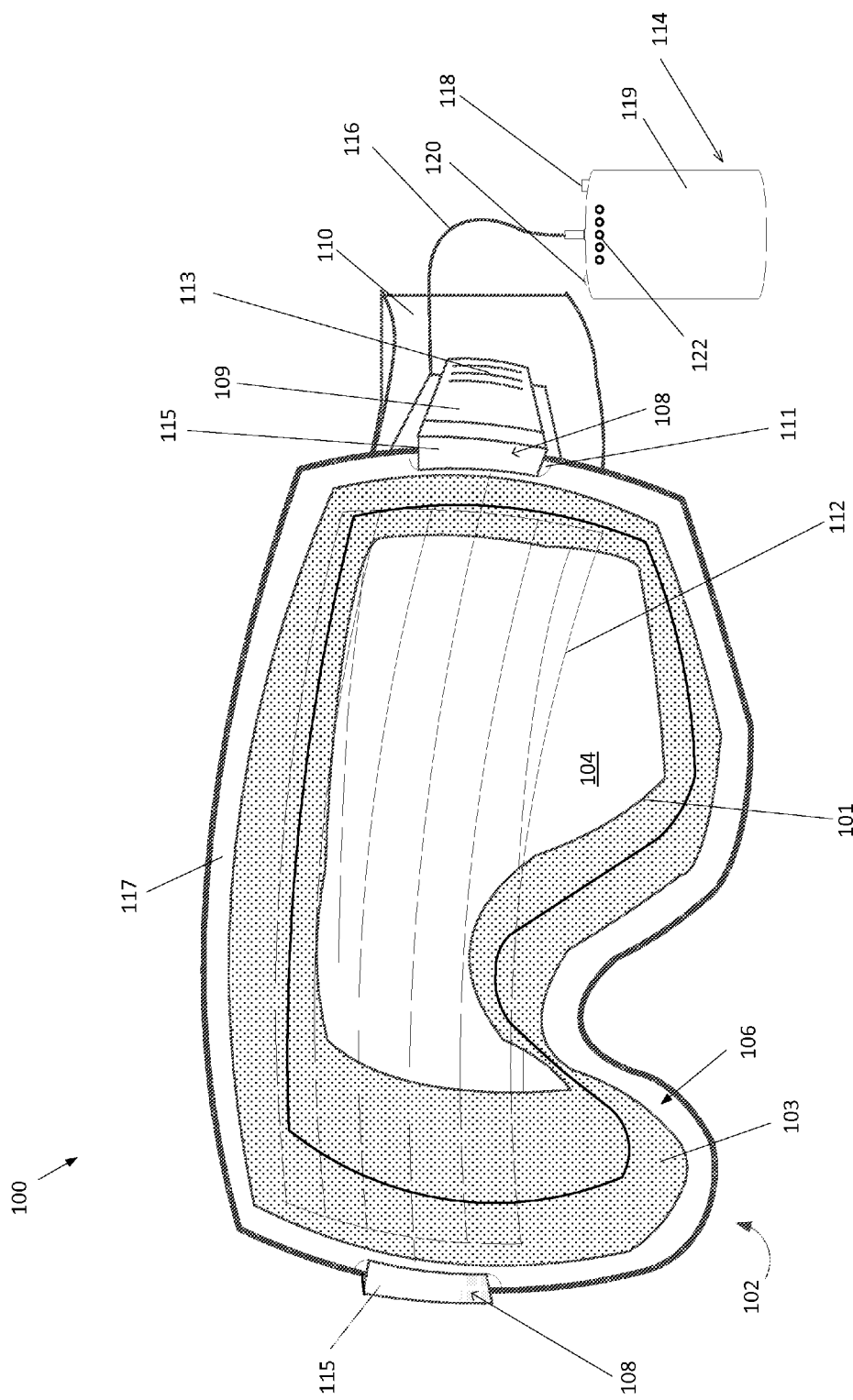
FIG. 1 is a perspective view of an anti-fog, interchangeable-lens goggle in accordance with an embodiment of the invention.

Referring to FIG. 1, there are shown interchangeable lens goggle components for an embodiment of an interchangeable lens goggle 100 that comprises a body 102, an easily interchangeable lens 104, a lens-to-body engagement mechanism 106, an optional interconnection means or mechanism 108 and a strap 110 all providing a goggle that enables easy adaptation to varying weather, lighting and goggle fogging conditions.

Figure 2:
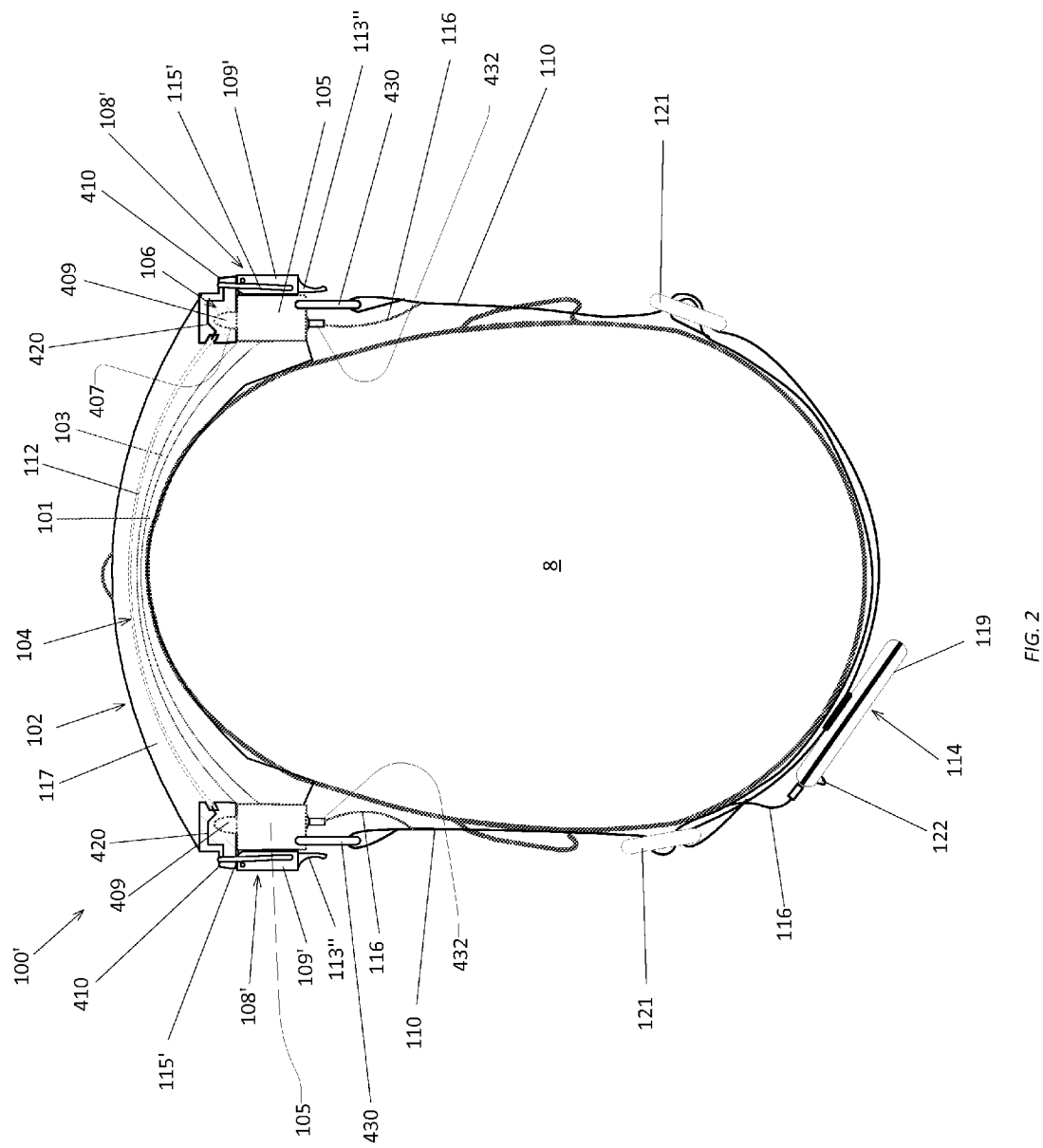
FIG. 2 is a top plan view of the goggle of FIG. 1 shown strapped on a user's head and with a water-proof battery pack attached to a strap portion of the goggle.

Used as an anti-fog goggle 100, the lens 104 of the goggle further comprises resistive-wire anti-fog means 112 that is connected to a water-proof power supply 114 via a power supply cable 116. Referring to FIG. 7, the power supply 114 may be suitably comprised of a lithium-ion, or lithium-poly, battery conventionally used in cell-phones, the battery being housed in a plastic-waterproof case 119 with an O-ring seal 710 and a rotatable clip 701 for attachment to clothing or a goggle strap 110 as shown in FIG. 2. Preferably, the battery 114 includes an on-off switch 118, a battery-life indicator switch 120 and battery-life indicia 122, such as varied color indicator LEDs, for demonstrating battery strength to the user of the goggle 100. The lens 104 further comprises a lens frame 117 which comprises an anterior portion, or surface, of engagement mechanism 106, the engagement mechanism 106 comprising any releasable attachment mechanism such as a horizontally disposed tongue-and-groove engagement mechanism as shown in FIG. 4a, or a cap-and-ridge engagement mechanism as shown in FIG. 6.

Body 102 comprises a posterior flexible portion 101, including foam or rubber-type materials for interfacing with the use's face as known in the art and an anterior more rigid, in effect semi-rigid, lightweight plastic, or other suitable material, portion 103 for interfacing with the lens 104. The posterior flexible portion 101 of the body 102 engages the user's face around the user's eyes and on the bridge of the user's nose, and the body 102 further comprises an anterior periphery around which is installed part of the engagement mechanism 106, whether it be the tongue part 409 of a tongue-and-groove engagement mechanism as shown in FIG. 4a, or whether it be a ridge part 609 of a cap-and-ridge engagement mechanism as shown in FIG. 6. Whichever part of the engagement mechanism is on the periphery of the anterior portion 103 of the body 102, the corresponding engagement member is to be attached on the lens 104, as further described herein, and the two parts of the engagement mechanism 106 interface, engage and enable releasable, attachment of the lens to the body. This attachment may, but need not seal the lens 104 to the body 102. The lens 104 is adapted for engaging the semi-rigid anterior portion of the body 102 a distance from the user's eyes so as to provide a shield to the eyes.

Referring to FIG. 1, interconnection mechanism 108 comprises a draw latch 109 that hooks into preferably metalized indentations 111 on lens 104. A preferably metal thumb press portion 113 of the draw latch enables the user to push the draw latch down to interconnect the goggle body 102 and the lens 104. Not only does the draw latch 109 serve to reinforce engagement of the lens 104 on the body 102, but it further establishes an electrical connection between the anti-fog resistive means 112 on the lens and the battery-operated power source 114 via wire 116 and as further described herein in connection with FIG. 4a.

Referring now to FIG. 2, there are shown interchangeable lens goggle components for another embodiment of an interchangeable lens goggle 100' that comprises a body 102, an easily interchangeable lens 104, a lens-to-body engagement mechanism 106, an optional interconnection mechanism 108' and a strap 110 all providing a goggle that enables easy adaptation to varying weather, lighting and goggle fogging conditions. The strap 110 is shown attached to an outer body periphery portion 105 with a pair of swivel rings 430. Wiring 116 may be either detachable with an appropriate plug 432, or simply hard-wired to the outer body periphery portion 105 of the body 102.

The primary difference between the goggle 100 of FIG. 1 and the goggle 100' of FIG. 2, is that the buckle portion 115' of the draw latch 109' of the goggle 100' pivots on the draw latch, whereas the buckle portion 115 of the draw latch 109 of goggle 100 is integral with the draw latch. As a result, some of the internal workings of the draw latchs 109, 109' may be slightly different between the two embodiments, but their function to clamp onto a hook portion 111, 410 of the lens 104, in order to secure engagement of the lens 104 onto the body 102 of the goggle, and also thereby make the interconnection between the heating element anti-fog resistive means 112 of the lens 104, and the battery 114, is essentially the same with either embodiment.

Figure 3A:
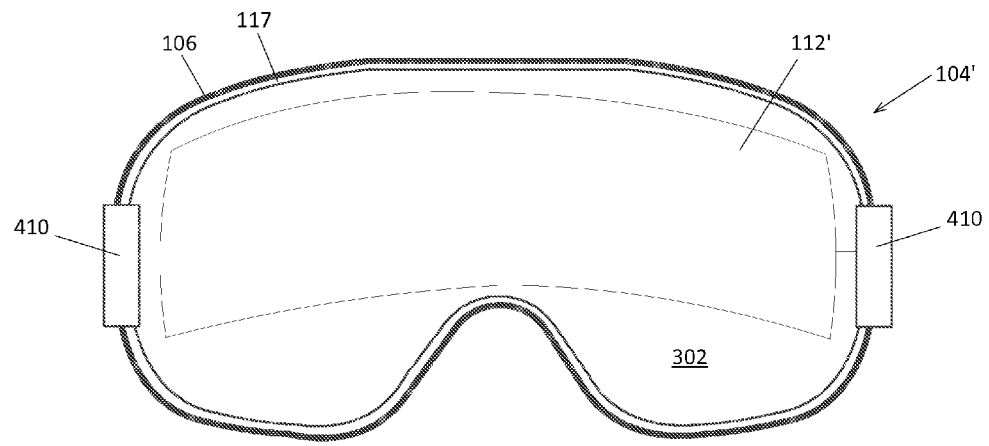
FIG. 3a is a front plan view of an un-tinted lens portion of the goggle of FIG. 1 and having resistive-coating anti-fog means thereon.
Figure 3B:
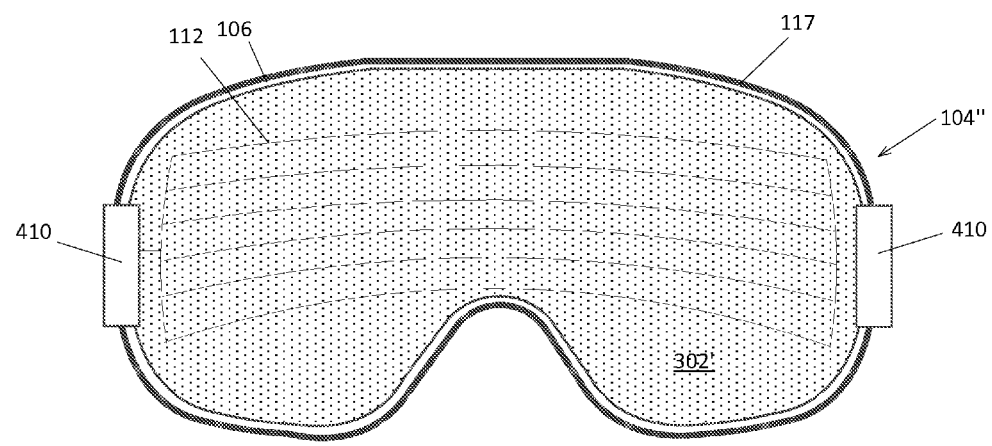
FIG. 3b is a front plan view of an alternate, tinted, lens portion of the goggle of FIG. 1 and having resistive-wire anti-fog means thereon.
Figure 3C:
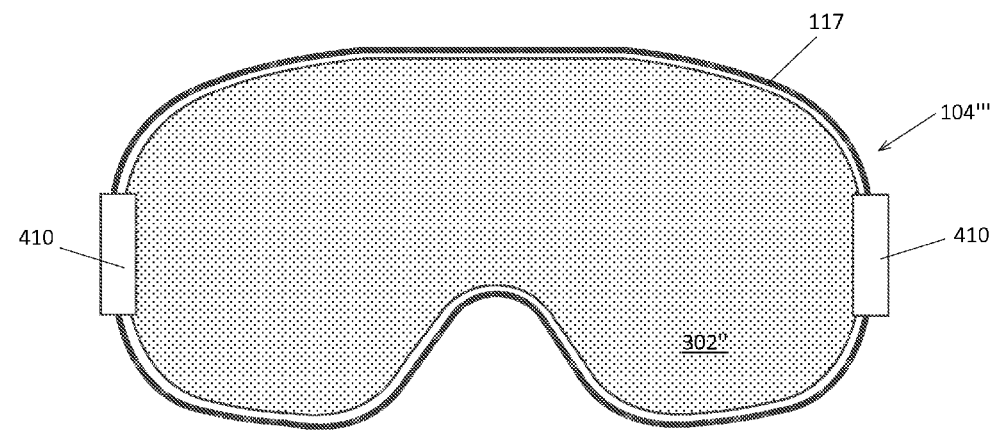
FIG. 3c is a front plan view of another alternate, differently tinted, lens portion of the goggle of FIG. 1 and not having anti-fog means thereon.

Referring now to FIGS. 3a-c, there are shown front plan views of lens portions of three different embodiments of the invention. FIG. 3a shows a lightly tinted, or un-tinted, lens portion 104' of a goggle in accordance with the invention and having resistive-coating, film, "gel" or layer anti-fog means 112' thereon. FIG. 3b shows an alternate embodiment, tinted lens portion 104" of a goggle in accordance with the invention and having resistive-wire anti-fog means 112 thereon. FIG. 3c shows another alternate embodiment, differently tinted, lens portion 104''' of a goggle in accordance with the invention and not having any battery-heated anti-fog means thereon.

Referring to FIGS. 2, 3a-c, 4a and 6, attachment of the tongue 409, groove 407 or ridge 609 portion of the engagement mechanism 106 to any of the lens portions 104, 104', 104", 104''' is accomplished through molding, gluing and/or physical pin/rivet type attachment means, it being the case that, where possible, the attachment of the tongue, groove or ridge may be preferably integrally formed with the lens frame portion 117, or molded around the entire periphery of the lens frame portion 117 in durable sealed fashion.

Referring more specifically to FIGS. 3a-c, a plurality of lenses of differing shade tints and differing anti-fog means characteristics are shown. The lens 104' of FIG. 3a comprises a clear lens surface 302, having an anti-fog resistive coating 112' included thereon with a clear backing, or double-lens construction as known in the art, to protect the anti-fog surface from being scratched off as may be necessary. The anti-fog resistive coating 112' preferably comprises an Indium Tin Oxide (ITO) compound that may be sprayed, deposited with a known ion-sputtering technique, painted or otherwise layered or applied. The film heating member 112' may be comprised of another material designed in the form of a resistive element that generates heat when connected to an electrical circuit without departing from the true scope and spirit of the invention.

Lens 104' further comprises interconnection/engagement hooks, plates or indentations 410 adapted for allowing a positive electrical connection via interconnection mechanism 108, or other interconnection mechanism disclosed hereafter, to the power source 114 via power supply cable 116. Lens 104' further comprises part of engagement mechanism 106, whether it be a tongue-and-groove type engagement mechanism, for example as shown at 407, 409 in FIG. 4a, where the part of the engagement mechanism 106 shown in FIG. 3a on the lens may comprise either the tongue or the groove, or a cap-and-ridge type engagement mechanism, for example as shown at 607, 609 in FIG. 6, where the part of the engagement mechanism 106 shown in FIG. 3a on the lens preferably comprises the cap. In either case, the part of the engagement mechanism 106 that that is associated with the lens 104' is interconnected to the lens and preferably extends around the entire periphery of the lens to allow formation of a complete, but releasable, attachment, or alternatively a seal, between the lens 104' and the body 102 of the goggle 100. Attachment of the tongue 409, groove 407 or cap 607 portion of the engagement mechanism 106 to the lens 104' is accomplished through molding, gluing and/or physical pin/rivet type attachment means, it being the case that, where possible, the attachment of the tongue, groove or cap may be preferably integrally formed with the lens surface 302, or tightly molded around the lens surface in durable fashion, as for example a seal with plastic or silicone.

Referring more specifically now to FIG. 3b, a lens 104" comprises a tinted lens surface 302', having an anti-fog resistive wire 112 included thereon with a clear backing, or double-lens construction as known in the art, to protect the anti-fog surface from being scratched off as may be necessary. Lens 104" further comprises interconnection/engagement hooks or plates 410 adapted for allowing a positive electrical connection via interconnection mechanism 108, or other interconnection mechanism described hereafter, to the power source 114 via power supply cable 116. Lens 104" further comprises part of engagement mechanism 106, whether it be part of a tongue-and-groove type engagement mechanism, for example as shown at 407, 409 in FIG. 4a, where the part of the engagement mechanism 106 shown in FIG. 3b on the lens may comprise either the tongue or the groove, or a cap-and-ridge type engagement mechanism, for example as shown at 607, 609 in FIG. 6, where the part of the engagement mechanism 106 shown in FIG. 3b on the lens preferably comprises the cap. In either case, the part of the engagement mechanism 106 that that is associated with the lens 104" is interconnected to the lens and preferably extends around the entire periphery of the lens to allow formation of a complete, but releasable, attachment, or alternatively a seal, between the lens and the body 102 of the goggle 100. Attachment of the tongue 409, groove 407 or cap 607 portion of the engagement mechanism 106 to the lens 104" is accomplished through molding, gluing and/or physical pin/rivet type attachment means, it being the case that, where possible, the attachment of the tongue, groove or cap may be preferably integrally formed with the lens surface 302', or tightly molded around the lens surface in durable fashion as with silicone or plastic.

Referring more specifically now to FIG. 3c, a lens 104''' comprises an alternate tinted lens surface 302", this time with no anti-fog resistive coating or wire included thereon, to show that use of a non-anti-fog lens with the goggles of the invention is allowable without damaging the system or even reducing battery life. This feature makes use of the goggle more care-free, as whether the battery is switched on, or off, the user is encouraged in choosing a goggle that suits the weather, terrain, and lighting conditions of the moment. While lens 104''' further comprises interconnection/engagement hooks or plates 410 adapted for allowing a positive electrical connection via interconnection mechanism 108, or other interconnection mechanism described hereafter, in the case where a non-anti-fog lens without wiring is installed, the interconnection mechanism does not establish an electrical connection to the power source 114 via power supply cable 116, but the interconnection mechanism still reinforces the engagement mechanism, depending upon the embodiment of the invention chosen, and as further described hereafter. Lens 104' further comprises part of engagement mechanism 106, whether it be part of a tongue-and-groove type for example as shown at 407, 409 in FIG. 4a, where the part of the engagement mechanism 106 shown in FIG. 3c on the lens may comprise either the tongue or the groove, or a cap-and-ridge type engagement mechanism, for example as shown at 607, 609 in FIG. 6, where the part of the engagement mechanism 106 shown in FIG. 3c on the lens preferably comprises the cap. In either case, the part of the engagement mechanism 106 that that is associated with the lens 104''' is interconnected to the lens and preferably extends around the entire periphery of the lens to allow formation of a complete, but releasable, attachment, or alternatively a seal, between the lens and the body 102 of the goggle 100. Attachment of the tongue 409, groove 407 or cap 607 portion of the engagement mechanism 106 to the lens 104''' is accomplished through molding, gluing and/or physical pin/rivet type attachment means, it being the case that, where possible, the attachment of the tongue, groove or cap may be preferably integrally formed with the lens surface 302", or tightly molded around the lens surface in durable fashion as with silicone or plastic.

Referring now more specifically to FIGS. 4a and 5a-c, an alternate embodiment goggle 100' is shown comprising a body 102, an easily interchangeable lens 104', lens-to-body engagement mechanism 106 comprising a tongue 409 and a groove 407, interconnection mechanism 108' and strap 110 all providing a goggle that enables easy adaptation to varying weather, lighting and goggle fogging conditions. The goggle body 102 and lens 104' of goggle 100' are comprised of similar materials to those corresponding components described in connection with goggle 100. The lens 104' is adapted for engaging the semi-rigid anterior portion of the body 102 a distance from the user's eyes so as to provide a shield to the eyes.

The goggle 100' would be used as an anti-fog goggle, since the lens 104' of the goggle 100' further comprises resistive-film anti-fog means 112 that is connected to a water-proof power supply 114 via a power supply cable 116. The power supply 114 comprises the same elements and features as further described herein.

Unlike the goggle 100 shown in FIG. 1, goggle 100' comprises a different style of interconnection mechanism 108' comprising a draw latch 109', or pressure latch, and hook 410 interconnection mechanism. The interconnection mechanism 108' serves to reinforce the tongue-and-groove engagement mechanism 407, 409 so that, for example during a fall encountered during more extreme physical activity, the lens 104' doesn't pop off on impact. Thus, the interconnection mechanism 108' may in one sense be seen as optional as shown in FIG. 4b, in that the engagement mechanism 407, 409 may be made with a tighter tolerance, or used for more sedate-type activity goggle wearing, in which case the engagement mechanism alone may be considered sufficient to engage the lens 104' with an outer periphery portion 105 of goggle body 102.

The interconnection mechanism 108' further serves to create an electrical connection between the resistive-film anti-fog means 112 within the composite lens 104' (e.g., comprising a main polycarbonate lens and a protective inner polymer coating) and the power supply 114 upon interconnection of the lens 104' and the body 102. Interconnection mechanism 108' comprises metal hooks 410 mounted on first and second outer ends of the lens 104'. These hooks 410 differ somewhat from comparable indentations 111 in FIG. 1 where the anterior portion 115 of interconnection mechanism 108 engages into the indentations. Interconnection mechanism 108' further comprises a draw latch 109' further comprising an alternate thumb press portion 113' and a buckle 115'. Resistive-film anti-fog means 112' is placed on lens 104' such that the resistive film 112' interconnects by electrical connection wire 420 passing through the lens frame 117. Buckle 115' is also metal, as is draw latch 109' (and preferably thumb press 113') such that interconnection of the buckle 115' with the metal hooks 410 reinforces the engagement mechanism 106 and simultaneously closes a circuit comprised of wiring 419, 116, resistive film 112' (or alternatively resistive wire 112), wire 420, metal hooks 410, latch or clip 115', draw latch 109' and thumb press 113'. This is similar in function to the interconnection mechanism 108. Thus, via interconnection mechanism 108', the lens 104' is secured to the body 102 simultaneously to when the electrical interconnection between the anti-fog resistive means 112 and the battery-operated power source 114 is securely made. Thus, this aspect of the invention facilitates a minimum of steps, at most one or two steps, for interconnection of a new lens 104 with the power source 114 such that users will be encouraged to use the same while engaging in the activity for which the goggle has been designed.

In this way, the interconnection mechanism 108' that is used to reinforce engagement of the lens 104' by engagement mechanism 106, including groove 407 and tongue 409, also completes the above-described circuit, simultaneously with the reinforcement of the lens.

The tongue-and-groove engagement mechanism 409, 407 of the engagement mechanism 106, wherein the tongue 409 is shown depending from an anterior periphery portion 103 of the body 102, is shown with the tongue being formed onto or attached to the anterior periphery portion of the body as further described herein. The groove 407 of the tongue-and-groove engagement mechanism 106 is formed into the lens frame 117.

The strap 110 may comprise a conventional adjustable elastomeric strap that is stretchy, and yet resilient, so as to allow comfortable retention of the goggle 100' on the user's head or a helmet 8 as shown in FIG. 2. The strap is adjustable via adjustment members 121. Further, the waterproof battery case may be sewn into the strap 110 or otherwise retained on or within the strap.

Referring specifically to FIG. 5a, operation of the interconnection mechanism 108" comprising a draw latch 109" is illustrated. In FIG. 5a, a user is free to remove the lens 104', because the latch or clip 115 is not engaged on the hook 410 on the lens. If the user wants to interconnect the groove 407 of the lens 104' with the tongue 409 of the body 102 and close the herein-described electrical circuit, he or she must raise the thumb press 113" of the draw latch 109" and place the latch 115 in the hook 410 as shown in FIG. 5b. Once this has been accomplished, he or she may press on the thumb press 113" and close the draw latch 109" as shown in FIG. 5c such that the lens 104' is reinforced on the tongue 409 of the body 102 and the circuit is completed to allow power to the resistive elements 112 on or in the lens 104'.

Referring now to FIG. 4b, an alternate embodiment of the invention is disclosed wherein there is shown a goggle 100". Like goggles 100' and 100, goggle 100" also comprises a body 102', further comprising an outer periphery 105', an anterior portion 103' and a posterior portion 101' for engaging the user's face, a lens 104", further comprising a lens frame 117", and a strap 110. An engagement mechanism 106 is also disclosed with this embodiment of the invention and which comprises tongue 409 and groove 407. Like other embodiments of the invention, lens 104" comprises a lens surface 302 having particular tint characteristics as desired, and further comprising resistive lens wiring 112 or film 112'. Similar to goggles 100 and 100', with goggle 100" an electrical connection is simultaneously made between the resistive-lens wiring 112, or alternatively resistive-film 112', and a battery power source 114 housed in a waterproof case 119, having an on/off switch 118, remaining battery life switch 120 and battery life indicia 122, when the posterior portion of lens 104" is installed on the anterior portion 103' of the body 102'.

The primary difference between goggle 100" and goggles 100, 100', is that goggle 100" of FIG. 4b does not include a draw latch type reinforcing interconnection mechanism. However, the tongue 409 and groove 407 may be made with a stronger interconnection component between them to reinforce engagement between the tongue and the groove. The goggle body 102' and lens 104" of goggle 100" are comprised of similar materials to those described in connection with goggle 100. The lens 104" is adapted for engaging the semi-rigid anterior portion of the body 102' a distance from the user's eyes so as to provide a shield to the eyes.

There is an interconnection mechanism for interconnection of wiring 112, or film 112', with battery source 114 included with goggle 100". The electrical interconnection for the anti-fog means 112, or other electrical needs such as a heads up display system, comprises the fact that the inner surface of groove 407 is metalized and connecting to the wiring 112, or film 112', while the tongue 409 is also metalized, to allow an electrical connection between them and the battery 114 via wires 419 and 116.

Referring now to FIG. 4c, yet another alternate embodiment of the invention is disclosed wherein there is shown a goggle 100'''. Like the other goggles comprising this invention, goggle 100''' also comprises a body 102", with an outer periphery 105", a lens 104", further comprising a lens frame 117", and a strap 110. An engagement mechanism 106 is also disclosed with this embodiment of the invention and which comprises tongue 409 and groove 407. Like other embodiments of the invention, lens 104" comprises a lens surface 302 having particular tint characteristics as desired, and further comprising resistive lens wiring 112 or film 112'. The goggle body 102" and lens 104" of goggle 100''' are comprised of similar materials to the similar components described in connection with goggle 100. The lens 104" is adapted for engaging the semi-rigid anterior portion of the body 102" a distance from the user's eyes so as to provide a shield to the eyes.

Similar to goggles 100, 100', 100", with goggle 100''' an electrical connection is simultaneously made between the resistive-wire 112, or alternatively resistive-film 112', and a battery power source 114 housed in a waterproof case 119, having an on/off switch 118, remaining battery life switch 120 and battery life indicia 122, when the posterior portion of lens 104" is installed on the anterior portion 103 of the body 102'.

Goggle 100'" of FIG. 4c further comprises a gate-type latch reinforcing interconnection mechanism 106" further comprising a pivotable base member 450 depending from and pivotable relative to the body 102" on pivot 454, and a finger member 452. The gate latch interconnection mechanism 106" snaps into place on the body when a far end of the finger member engages the frame 117" or the surface 302 or 302' of lens 104", biasing the lens 104" so that not only is the lens held in place, but an electrical connection is also established between metalized inner surface 411 of the groove 407 and the metalized surface 417 of the post 409, the groove being interconnected with the resistive heater element 112 and the post being interconnected with the wiring 419, which is in turn connected to wiring 116 and the battery 114.

Referring now to FIG. 4d, a goggle 100"" also comprises a gate-type latch reinforcing interconnection mechanism 106" as described in connection with FIG. 4c, which further comprises a pivotable base member 450 depending from and pivotable relative to the body 102" on pivot 454, and finger member 452. The gate latch interconnection mechanism 106" snaps into place on the body 102" when a far end of the finger member engages the frame 117'" or the surface 302", biasing the lens 104'" so that the lens is held in place. With this embodiment of the goggle, no electrical connection is established between a resistive heater element 112, 112' and a battery source 114, since there is no heater element 112, 112' in lens 104'".

This embodiment of FIG. 4d illustrates the fact that while a switch 118 on battery 114 may be employed either on, or off, when the battery is not in use, placing a non-anti-fog lens in the goggle will not damage or unduly run down the battery. The embodiment of FIG. 4d also illustrates how various types of lenses may be interchanged with different goggle bodies employing different engagement and interconnection mechanism without departing from the true scope and spirit of the invention.

Referring now to FIG. 4e, an alternate embodiment goggle 468 is shown comprising a peripheral inner lens frame 470 further comprising a semi-rigid to semi-flexible anterior portion 475 for retaining a lens 476 and a softer, flexible, foam-rubber-like, posterior portion 479 for ready engagement with a user's face adjacent the eyes and bridge of the nose as a single, open goggle enclosure.

The lens frame 470 defines a groove 474, that is at least partially metallized for electrical contact purposes, serving as part of a peripheral tongue-and-groove lens/body engagement member 480. The lens 476 is retained in the inner lens frame 470 and has placed thereon a resistive, anti-fog, heating element 482, such as a resistive-film heating element or resistive-wire heating element, the resistive heating element being electrically connected with the metalized groove 474 at 477. The goggle 468 further comprises an anterior, peripheral, semi-rigid to semi-flexible body member 484 having first and second ends and further comprising a peripheral tongue 486, that is at least partially metallized for electrical contact purposes, for engagement with the groove 474. The tongue 486 being electrically connected at 487 with a wire 488 through an end 465, 467 of the body member 484 to a battery 490 also housed within the body member. The goggle body member 484, lens frame 470 and lens 476 of goggle 468 are comprised of similar materials to those similar components described in connection with goggle 100. The lens 476 is held a distance from the user's eyes by the lens frame 470 so as to provide a shield to the eyes.

The battery 490 connection to the resistive element 482 has an on/off switch 492 carried on the body, and there is a battery test button 494 carried on the body, and a battery strength indicator 495 also carried on the body. Upon depressing the on/off switch 492, the battery strength indicator 495, and a heat, or power level, indicator 499, are shown and displayed preferably within the goggle 468 to the user of the goggle. Goggle 468 further comprises a strap 496 attached via connectors 463 to the ends 465, 467 of the body 484 for holding the goggle on the user's head or helmet. The peripheral tongue 486 and groove 474 clearance may optionally be of a fit that holds the peripheral tongue and groove slightly apart, as may be accomplished with a slight detent in the tongue and/or groove, so as to not make electrical contact between the resistive element 482 and the battery 490 until the user has placed the goggle on his or her head such that the strap 496 overcomes the optional spring bias or detent between the tongue and the groove. Alternatively, the tongue 486 and groove 474 clearance may be of a fit that biases the electrical contacts in each together regardless of whether the strap 496 is installed on a user's head. Of course, the goggle 468 may use a resistive wire or resistive film anti-fog means, or alternatively no anti-fog means, in the lens 476 thereof.

Referring now to FIG. 4f, a goggle 500 is shown comprising an outer lens frame 502 preferably made of plastic, silicone or other resilient, or alternatively tacky or stretchy, material, which surrounds the periphery of a lens 504. Lens 504 has either a resistive wire 112, or resistive film 112' anti-fog means heating element thereon. On each end 503, 505 of the lens 504 there is a loop, or band, 506, 508 of stretchy, preferably silicone, material serving as an interconnection mechanism 506, 508, for reinforcing engagement of the lens. Loop/band interconnection mechanism 508 preferably further comprises a pull tab 510 at the furthest extent of the loop/band to facilitate easy grabbing, installation and removal of the loop/band interconnection mechanism from the lens frame 502.

Goggle 500 further comprises a goggle peripheral body 512 preferably made of plastic that is semi-flexible, but resilient. On each end 511, 513 of the plastic body 512 is a post 514, 515, respectively, each post having a channel 516, 517, respectively, formed around the post and adapted to receive and retain the corresponding stretchy silicone loop/band 506, 508. While the goggle lens frame 502 may be made of plastic or silicone, the goggle body 512 and lens 504 of goggle 500 are comprised of similar materials to those described in connection with goggle 100. The lens 504 is adapted for engaging the semi-rigid anterior portion of the body 512 a distance from the user's eyes so as to provide a shield to the eyes.

The lens frame 502 further comprises a pair of contacts 526, 528, one contact at either end of the lens frame, and the goggle body 512 further comprises a pair of contacts 530, 532, one contact preferably being provided on an anterior portion of each post 514, 515. Depending from either end 511, 513 of the goggle body 512, the goggle 500 further comprises a silicone strap extension member 520, 522, respectively. Upon stretching the bands 506, 508 around their respective posts 514, 515, engagement of the lens frame 502 on the goggle body 512 is assured, and an electrical connection is made between the resistive-film anti-fog means 112' and a battery 519 carried internally of the goggle body 512, or alternatively in the strap extension members 520, 522. The electrical connection is made via contacts 526, 528 on the lens frame 502 and contacts 530, 532 on the posts 514, 515, respectively, of the goggle body 512.

As with other embodiments of the goggle of the present invention, the goggle 500 further comprises a posterior foam rubber interface member 524 attached to a posterior portion of the goggle body 512, such as by gluing, providing a comfortable interface of the goggle 500 on a user's face, and a textile strap portion 507 for assisting with retention of the goggle on a user's head or helmet.

Goggle 500 further comprises a button 534, 536 on each end 511, 513, respectively, of the goggle body 512, preferably on posts 514, 515, respectively, for controlling on/off and heat level of the anti-fog means 112, or 112', on the lens 504. Upon depressing the on/off button 534, heat source 519 is switched on. Alternatively, a battery-strength indicator (not shown), and a heat, or power level, indicator (not shown), may be displayed preferably within the goggle 500 to the user of the goggle. Depressing the on/off button 534 again turns off the heat, or more accurately reduces it to an extremely low power state. Depressing the button 536 adjusts the power level applied to the anti-fog means 112', (or alternatively 112 not shown) and also causes the power level display 540 to indicate the level of power being applied to the anti-fog means. After a short time, preferably, the indicators 538 and 540 turn off so as to not unduly distract the user. The circuitry 588 also interconnects a standard USB or other power connector charging receptacle 575, the battery 519, logic for controlling power on/off, power level increase/decrease, power level indication, and battery level indication using electric light pipes, for example.

Referring now to FIG. 4g, there is provided an alternate embodiment goggle 600 in accordance with the present invention. The goggle 600 comprises a body 612, having ends 611, 612 with silicone extension members 620, 622 depending therefrom. The goggle body 612 further comprises a plurality of attachment receptacles 605, at least one attachment lower lip 603 and a battery power source 619 internal of the goggle body 612. The power source 619 may be alternatively carried on the silicone extension members 620, 622. Goggle 600 further comprises a separate lens 604 having resistive-film/coating anti-fog means 112', or alternatively resistive-wire anti-fog means 112 thereon. Contacts 624, 626 are provided on goggle body 612, and corresponding contacts 628, 630 are provided on lens 604 for enabling interconnecting of the resistive heating means 112' of the lens with the battery power source 619. An outer face member 602 is provided for interconnecting the lens 604 with the goggle body 612, the outer face member being preferably made of silicone and having a lower outer lip 632 for releasably engaging the lower lip 603 of the goggle body. The outer face member 602 further comprises an upper nub 635 and side nubs 635 for insertion in attachment receptacles 605 of the goggle body 612, thus interconnecting the silicone face member and the goggle body with the lens being interposed and held in place between the goggle body and the silicone face member. While the goggle face/skin 602 is preferably comprised of silicone, the goggle body 612 and lens 604 of goggle 600 are comprised of similar materials to those described in connection with goggle 100. The lens 604 is adapted for engaging the semi-rigid anterior portion of the body 612 a distance from the user's eyes so as to provide a shield to the eyes.

The anti-fog means 112' on the lens 604 thus makes contact with the goggle body 612 via contacts 624, 626, 628, 630.

Electrical circuitry 688 like that shown in connection with FIG. 4e is provided within the goggle body 612 of goggle 600, with contacts (e.g., buss bars) 628, 630 on the lens 604 being similar to contacts 477 shown in FIG. 4e, and contacts 624, 626 on the goggle frame being similar to contacts 487 shown in FIG. 4e, with wiring 688 running through the goggle body 612 to interconnect the resistive-film heating means 112', the battery 619, the USB, or other power connection, charging receptacle 675, the on/off button 634, the power level adjustment button 636 and the indicators 638, 640.

As with other embodiments of the goggle of the present invention, the goggle 600 further comprises a posterior foam rubber interface member 625 attached to a posterior portion of the goggle body 612, such as by gluing, providing a comfortable interface of the goggle 600 on a user's face. The goggle 600 also preferably comprises a textile strap portion 607. The goggle body 612 may also include vents 621 therein to assist with ventilation for removal of condensate and fogging, in case the battery 619 has died, or in the case of a lens 604 not having anti-fogging means 112', or 112, thereon.

Goggle 600 further comprises a button 634, 636 on each end 611, 613, respectively, of the goggle body 612, for controlling on/off and heat level of the anti-fog means 112, or 112', on the lens 604. Upon depressing the on/off button 634, the power source 619 is switched on (into the circuit), and a battery strength indicator 638 and a heat, or power level, indicator 640, are displayed preferably within the goggle 600 to the user of the goggle. Depressing the on/off button 634 again turns off the heat, or more accurately reduces it to an extremely low power state. Depressing of the button 636 adjusts the power level applied to the resistive-coating/film anti-fog means 112', or alternatively resistive-wire anti-fog means 112 (not shown), and also causes the power level display 640 to indicate the level of power being applied to the anti-fog means. After a short time, preferably, the indicators 638 and 640 turn off so as to not unduly distract the user. The circuitry 688 also interconnects a preferably standard USB charging receptacle 675, the battery 619, logic for controlling power on/off, power level increase/decrease, power level indication, and battery level indication using electric light pipes, for example.

Referring now to FIG. 4h, a goggle 700 that is similar to goggle 600 of FIG. 4g is shown. Like goggle 600, goggle 700 has a goggle body 712 having silicone extension members 720, 722 depending therefrom. Goggle 700 comprises a plurality of attachment slots 705, finger depression detachment aids 706, an attachment lower lip 703 and a battery power source 719 carried on the silicone extension members 720, 722, or alternatively internal of the goggle body 712. Goggle 700 further comprises a separate lens 704 having resistive-wire anti-fog means 112 or resistive-film anti-fog means 112' thereon. Contacts 724, 726 are provided on goggle body 712, and corresponding contacts 728, 730 are provided on lens 704 for enabling interconnecting of the lens with the battery power source 719. An outer pop-off face member 702 is provided for interconnecting the lens 704 with the goggle body 712, the outer pop-off face member made of plastic and having a plurality of attachment prongs 732 for releasably engaging the outer pop-off face member with the goggle body. In this way, the outer pop-off face member 702 and the goggle body 702 are interconnected with the lens 704 being interposed and held in place between the goggle body and the outer pop-off face member. While the outer pop-off face member 702 may be comprised of silicone, the face member, the goggle body 712 and lens 704 of goggle 700 are comprised of similar materials to those corresponding components described in connection with goggle 100. The lens 704 is adapted for engaging the semi-rigid anterior portion of the body 712 a distance from the user's eyes so as to provide a shield to the eyes.

The anti-fog means 112' on the lens is also held in place relative to the goggle body 712 by the pop-off face member 702, and the anti-fog means thus makes contact with the goggle body via contacts 724, 726, 728, 730.

Electrical circuitry like that shown in connection with FIG. 4e is provided within the goggle body 712 of goggle 700, with contacts (e.g., buss bars) 728, 730 on the lens 704 being similar to contacts 477 shown in FIG. 4e, and contacts 724, 726 on the goggle frame being similar to contacts 487 shown in FIG. 4e, with wiring 788 running through the goggle body 712 to interconnect the resistive heating means 112', the battery 719, the USB, or other power connection, recharging receptacle 775, the on/off button 734, the power level adjustment button 736 and the indicators 738, 740.

As with other embodiments of the goggle of the present invention, the goggle 700 further comprises a posterior foam rubber interface member 725 attached to a posterior portion of the goggle body 712, such as by gluing, providing a comfortable interface of the goggle 700 on a user's face. The goggle 700 also preferably comprises a textile strap portion 707.

Goggle 700 further comprises a button 734, 736 on each end 711, 713, respectively, of the goggle body 712, for controlling on/off and heat level of the anti-fog means 112, or 112', on the lens 704. Upon depressing the on/off button 734, the battery 719 is switched on (i.e., into the circuit) to provide power to the resistive heating means 112', a battery strength indicator 738, and a heat, or power level, indicator 740, are displayed preferably within the goggle 700 to the user of the goggle. Depressing the on/off button 734 again turns off the heat, or more accurately reduces it to an extremely low power state. Depressing of the button 736 adjusts the power level applied to the anti-fog means 112, or 112', and also causes the power level display 740 to indicate the level of power being applied to the anti-fog means. After a short time, preferably, the indicators 738 and 740 turn off so as to not unduly distract the user. The circuitry 788 also interconnects a preferably standard USB charging receptacle 775, the battery 719, logic for controlling power on/off, power level increase/decrease, power level indication, and battery level indication using electric light pipes, for example.

Referring now to FIG. 4i, an alternative embodiment goggle 800 is disclosed comprising a goggle body 812 having ends 811, 813 with a textile strap 807 depending therefrom. The goggle body 812 has formed therein a plurality of attachment clip receptacles 805 and a battery power source 819 internal of the goggle body. Goggle 800 further comprises a lens 804 integrated onto a pop-off back frame 809, the back frame 809 being attachable and releasable from the goggle body 812, the lens having resistive-film anti-fog means 112', or alternatively resistive-wire anti-fog means 112, thereon. Power connector receptacles 824, 826 are provided on the goggle body 812, and corresponding power connectors 828, 830 are provided on the pop-off back frame 809 for enabling interconnecting of the resistive anti-fog means 112' of the lens 804 with the battery power source 819. Depending from and attached to a posterior portion of the pop-off back frame 809 there are a plurality of depression snap fit clips 835 for insertion in corresponding attachment receptacles 805. Thus engaged, the pop-off back frame 809 and the goggle body 812 are releasably interconnected, and the anti-fog means 112' of the lens 804 is electrically interconnected to the battery 819 on the goggle body 812 via power connector sockets 824, 826 and power connectors 828, 830. The lens 804 and lens back frame 809 are held in place on the goggle body by the snap fit clips 835 retained by hooks on the clips within the corresponding attachment receptacles 805. Removal assist indentations 801 may be employed to help in separation of the back frame 809 from the goggle body 812. The goggle body 812, the lens back frame 809 and the lens 804 of goggle 800 are comprised of similar materials to corresponding components (the lens back frame 809 roughly corresponding to the engagement mechanism 106 described in connection with goggle 100. The lens 804 is adapted for engaging the semi-rigid anterior portion of the body 812 a distance from the user's eyes so as to provide a shield to the eyes.

Electrical circuitry similar to that shown in connection with FIG. 4e is provided within the goggle body 812 of goggle 800, with power connectors 828, 830 on the lens back frame 809 being similar to contacts 477 shown in FIG. 4e, and power connector receptacles 824, 826 on the goggle frame being similar to contacts 487 shown in FIG. 4e, with wiring 888 running through the goggle body 812 and lens back frame 809 to interconnect the resistive heating means 112', the battery 819, the USB, or other power connection, recharging receptacle 875, the on/off button 834, the power level adjustment button 836 and the indicators 838, 840.

Goggle 800 further comprises a plurality of buttons 834, 836 on end 811 of the goggle body 812, for controlling on/off and heat level of the anti-fog means 112, or 112', on the lens 804. Upon depressing the on/off button 834, a battery strength indicator 838, and a heat, or power level, indicator 840, are displayed preferably within the goggle 800 to the user of the goggle. Depressing of the button 836 adjusts the power level applied to the anti-fog means 112, or 112', and also causes the power level display 840 to indicate the level of power being applied to the anti-fog means. After a short time, preferably, the indicators 838 and 840 turn off so as to not unduly distract the user. The circuitry 888 also interconnects a preferably standard USB charging receptacle 875, the battery 819, logic for controlling power on/off, power level increase/decrease, power level indication, and battery level indication using a series of electric light pipes, for example.

Referring now to FIG. 4j, there is shown a goggle 900, having a goggle body 912 with ends 911, 913 and silicone extension members 920, 922 depending in a flexible manner from each end 911, 913, respectively, and a textile strap 907 depending from each silicone extension member. Goggle 900 has a plurality of attachment receptacles 905 formed on an anterior front surface in the goggle body 912 and a battery power source 919 carried in the silicone extension members 920, 922, or alternatively, internal of the goggle body 912 (not shown). Goggle 900 further comprises a lens 904 carried in a peripheral pop-off lens frame 909 and having resistive-film anti-fog means 112', or alternatively resistive-wire anti-fog means 112, thereon. Contacts 924, 926 are provided on goggle body 912, and corresponding contacts 928, 930 are provided on lens 904 for enabling interconnecting of the lens with the battery power source 919 through connectors 997, 998. An outer peel-off silicone face member/skin 902 is provided for covering the pop-off lens frame 909, the outer peel-off silicone face member/skin comprising an inner lip 950 around the a posterior periphery thereof for engaging an outer lip 952 on the periphery of the pop-off lens frame 909 and comes in a variety of colors and patterns for style purposes. While the outer peel-off face member 902 is preferably comprised of silicone, the pop-off lens frame 909, the goggle body 912 and lens 904 of goggle 900 are comprised of similar materials to those corresponding components described in connection with goggle 100. The lens 904 is adapted for engaging the semi-rigid anterior portion of the body 912 a distance from the user's eyes so as to provide a shield to the eyes.

The pop-off lens frame 909 further comprises a plurality of attachment prongs 932 with finger depressions 933 for releasably engaging the pop-off lens frame with the attachment receptacles 905 on the goggle body 912 thus interconnecting the pop-off lens frame member and retained lens 904 and the goggle body with the lens being releasably held in place on the goggle body 912. Thus held in place by the attachment prongs 932 engaged in the attachment receptacles 905, the anti-fog means 112' on the lens is enabled and reinforced in making contact with the goggle body via contacts 924, 926, 928, 930.

Goggle 900 further comprises a plurality of buttons 934, 936 on end 911, 913, respectively, of the goggle body 812, for controlling on/off and heat level of the anti-fog means 112, or 112', on the lens 904. Upon depressing the on/off button 934, power to the anti-fog means 112' is supplied by switching the battery into the circuit, a battery strength indicator 938, and a heat, or power level, indicator 940, are displayed preferably within the goggle 900 to the user of the goggle. Pressing the on/off button 934 again turns the battery off, or more accurately reduces it to a very low, negligible, power state. Depressing of the button 936 adjusts the power level applied to the anti-fog means 112, or 112', and also causes the power level display 940 to indicate the level of power being applied to the anti-fog means. After a short time, preferably, the indicators 938 and 940 turn off so as to not unduly distract the user. Electrical circuitry 999 also interconnects a USB or other standard charging receptacle 975, the battery 919, logic for controlling power on/off, power level increase/decrease, power level indication, and battery level indication using a series of electric light pipes, for example.

The electrical circuitry 999 is similar to that shown in connection with FIG. 4e is provided within the goggle body 912 of goggle 900, with contacts 928, 930 on the lens 904 being similar to contacts 477 shown in FIG. 4e, and contacts 924, 926 on the goggle body being similar to contacts 487 shown in FIG. 4e. Wiring 999 runs through the goggle body 912 between the battery 919 and the resistive-coating/film heating means 112', or alternatively resistive-wire heating means 112 (not shown). As with all other embodiments of the invention, the circuitry 999 also interconnects a standard USB, or other standard charging, receptacle 975, the battery 919, on/off button, power level increase/decrease, power level indication, and battery level indication using a plurality of light pipes, for example.

As with other embodiments of the goggle of the present invention, the goggle 900 further comprises a posterior foam rubber interface member 925 attached to a posterior portion of the goggle body 912, such as by gluing, providing a comfortable interface of the goggle 900 on a user's face. The goggle 900 also preferably comprises a textile strap portion 907.

Referring now to FIG. 4k, there is shown a front perspective view of a goggle in accordance with the present invention for purposes of illustrating where the section is taken for FIGS. 4a-4e. The section line on FIG. 4k may also be used as a reference to show generally where the sections for FIGS. 5a-5c and FIG. 6 are taken.

Referring now to FIG. 6, an alternate embodiment of the invention is disclosed comprising a cap-and-ridge version of a goggle 650. Goggle 650 comprises a lens 652 having a heating element 654 thereon, or therein. The heating element is electrically connected with wire 656 that runs through lens frame 658 which terminates in a cap edge 607. Lens 652 is of a size and shape that the periphery thereof corresponds with the periphery of a body member 670 which terminates in a ridge portion 609 adapted for receiving and releasably holding the cap edge 607 along the periphery of each the cap and the ridge. Wire 658 in lens frame 658 which terminates at contact 660. The lens 652 and the lens frame 658 may be an integral unit made of plastic, or the frame may be installed around the periphery of the lens. The goggle 650 further comprises a goggle body 670 preferably made of a flexible, but resilient, plastic material. As with other embodiments of the invention, the goggle body 670 further comprises at its posterior a foam-rubber-type interface 621 for interfacing the goggle 650 with a user's face. Goggle body 670 further comprises contact 662 and wiring 419.

Contact 660 is positioned so as to make electrical contact with contact 662, which in turn is connected through the wire 419 embedded in body 670 and wire 116 leading out of the body through optional plug 663 and into the battery 114 via the strap 110. When a user wishes to change lens 652, he or she simply peels the lens off and replaces it with another lens, thus easily engaging the lens 652 with the body 670, the user thus automatically and simultaneously making the described electrical condition for the purpose of heating the goggle lens 652 with heating element 654 to provide anti-fogging capability.

While a preferred embodiment of the present invention has been shown and described, it will be apparent to those skilled in the art that many changes and modifications may be made without departing from the invention in its broader aspects. For example, it will be appreciated that one of ordinary skill in the art may mix and match the various components of the various embodiments of the invention without departing from the true spirit of the invention as claimed. Thus, by way of example, it will be appreciated that a cap-and-ridge engagement mechanism may be interchanged with a tongue-and-groove engagement mechanism in any embodiment without departing from the scope of the invention. Further, interchanging lens colors or disclosed anti-fog capability with alternate embodiment body or lens frame would likewise not depart from the spirit and scope of the invention. The appended claims are therefore intended to cover all such changes and modifications as fall within the true spirit and scope of the invention.

What is claimed is:

1. An anti-fog, interchangeable-lens goggle adapted for use with a battery comprising:
   a body having first and second ends, a flexible posterior portion adapted for engaging a user's face at user's eyes and a bridge of a user's nose when worn and a semi-rigid anterior portion;
   a lens having an anti-fog heating element thereon, said lens adapted for engaging the semi-rigid anterior portion of said body a distance from the user's eyes so as to provide a shield to the eyes;
   a lens and body engagement mechanism, having a portion thereof attached to said lens and a portion thereof attached to said body, for releasably interconnecting said lens and the semi-rigid anterior portion of said body;
   a heating element and battery electrical interconnecting mechanism depending from said body adapted for detachably interconnecting the heating element of said lens and the battery, said interconnecting mechanism operable with said engagement mechanism such that interconnecting the heating element of said lens with the battery also reinforces interconnecting of said lens with the semi-rigid anterior portion of said body, and such that disconnecting the heating element and the battery also releases said lens for disengagement from the semi-rigid anterior portion of said body; and a strap having first and second ends, the first end of said strap interconnected with the first end of said body, and the second end of said strap interconnected with the second end of said body, adapted for holding the goggle on a user's head.

2. The anti-fog, interchangeable-lens goggle of claim 1, wherein said engagement mechanism further comprises cap-and-ridge members wherein the cap is on a periphery of the lens and the ridge is on a periphery of the anterior portion of the body.

3. The anti-fog, interchangeable-lens goggle of claim 1, wherein said interconnecting mechanism adapted for detachably interconnecting the heating element of said lens and the battery further comprises a hook on said lens and a latch pivotably mounted to said body for engagement with the hook of said lens, said latch operable to a first position to bias an end of said lens against said body, thus reinforcing attachment of said lens on said body, and to interconnect the heating element of said lens and the battery, said latch operable to a second position to release said lens for removal from said body and to disconnect the heating element of said lens from the battery.

4. The anti-fog, interchangeable-lens goggle of claim 1, wherein said interconnecting mechanism adapted for detachably interconnecting the heating element of said lens and the battery further comprises a pivotable latching gate on said body, said gate operable to a first position to bias an end of said lens against said body, thus reinforcing attachment of said lens on said body, and to interconnect the heating element of said lens and the battery, said gate operable to a second position to release said lens for removal from said body and to disconnect the heating element of said lens from the battery.

5. The anti-fog, interchangeable-lens goggle of claim 1, wherein said interconnecting mechanism adapted for detachably interconnecting the heating element of said lens and the battery further comprises an outer peripheral member having a plurality of interconnection members around an inner periphery of the peripheral member, and a corresponding plurality of receptacles defined around an outer periphery of said goggle body, each receptacle adapted for receiving and retaining a corresponding interconnection member in a first closed position to bias said lens on said body, thus reinforcing attachment of said lens on said body, and to interconnect the heating element of said lens and the battery, said interconnection members being operable to an open position disconnected from their corresponding receptacles to disconnect the heating element of said lens from the battery.

6. An anti-fog, interchangeable-lens goggle adapted for use with a battery comprising:
a body having a first end, a second end, a flexible posterior portion adapted for engaging a user's face and a bridge of user's nose at user's eyes when worn and having a semi-rigid anterior portion;
a lens having a first end, a second end and an anti-fog heating element thereon, said lens adapted for engaging the semi-rigid anterior portion of said body a distance from the user's eyes so as to provide a shield to the eyes;
a lens, body, heating element, and battery engagement mechanism adapted for interconnecting the anti-fog heating element of said lens with the battery, a part of the engagement mechanism being connected to said body and a part of the engagement mechanism being connected to said lens, said engagement mechanism being operable between first engaged and second disengaged positions, wherein operation of said engagement mechanism to the first engaged position releasably interconnects said lens with the semi-rigid anterior portion of said body and releasably interconnects the anti-fog heating element of said lens with the battery, and wherein operating of said engagement mechanism to the second disengaged position removes said lens from the semi-rigid anterior portion of said body and disconnects the anti-fog heating element of said lens from the battery; and
a strap having first and second ends, the first end of said strap interconnected with the first end of said body, and the second end of said strap interconnected with the second end of said body, said strap adapted for holding the goggle on a user's head and a face.

7. The anti-fog, interchangeable-lens goggle of claim 6, wherein said engagement mechanism further comprises cap-and-ridge members wherein the cap is on a periphery of said lens and the ridge is on a periphery of the anterior portion of said body.

8. The anti-fog, interchangeable-lens goggle of claim 6, further comprising an interconnection mechanism, a part of the interconnection mechanism being connected to said body and a part of the interconnection mechanism being connected to said lens, for reinforcement of engagement of said lens and the semi-rigid anterior portion of said body.

9. The anti-fog, interchangeable-lens goggle of claim 8, wherein said interconnection mechanism further comprises a plurality of hooks, at least one hook depending from the first end of said lens, at least one hook depending from the second end of said lens, said interconnection mechanism further comprising a plurality of latches, at least one latch being pivotably attached to the first end of said body, at least one latch being pivotably attached to the second end of said body, each said latch engaging with one of said hooks to releasably interconnect said lens with the semi-rigid anterior portion of said body and to releasably interconnect the anti-fog heating element of said lens with the battery in the first engaged position of each said latch, each said latch releasing said lens from the semi-rigid anterior portion of said body and disconnecting the anti-fog heating element of said lens from the battery-powered heat source in the second disengaged position of each said latch.

10. The anti-fog, interchangeable-lens goggle of claim 8, wherein said interconnection mechanism further comprises a plurality of latching gates, at least one gate being pivotably attached to the first end of said body, at least one gate being pivotably attached to the second end of said body, each said gate being operable to a first position to bias an end of said lens against said body, thus reinforcing attachment of said lens on said body, each said gate interconnecting the heating element of said lens and the battery, each said gate operable to a second position to release said lens for removal from said body and to disconnect the heating element of said lens from the battery.

11. The anti-fog, interchangeable-lens goggle of claim 8, wherein said interconnection mechanism adapted for detachably interconnecting the heating element of said lens and the battery further comprises an outer peripheral member having a plurality of interconnection members around an inner periphery of the peripheral member, and a corresponding plurality of receptacles defined around an outer periphery of said goggle body, each receptacle adapted for receiving and retaining a corresponding interconnection member in a first closed position to bias said lens on said body, thus reinforcing attachment of said lens on said body, and to interconnect the heating element of said lens and the battery, said interconnection members being operable to an open position disconnected from their corresponding receptacles to disconnect the heating element of said lens from the battery.

12. The anti-fog, interchangeable-lens goggle of claim 6, wherein said engagement mechanism further comprises a peel-off, horizontal tongue-and-groove engagement mechanism, one of the tongue-and-groove being attached around the periphery of said lens, the other of the tongue-and-groove being attached around the periphery of the semi-rigid anterior portion of said body, for releasably interconnecting said lens and the semi-rigid anterior portion of said body.

13. The anti-fog, interchangeable-lens goggle of claim 12, further comprising a latch depending from said body and operable between open and closed positions such that in the closed position the latch biases said lens onto the semi-rigid anterior portion of said body and thus reinforces the releasable interconnection of said lens and the semi-rigid anterior portion of said body, and in the open position of said latch said lens is released for removal from the semi-rigid anterior portion of said body.

14. The anti-fog, interchangeable-lens goggle of claim 6, wherein said engagement mechanism further comprises a peel-off cap-and-ridge engagement mechanism, one of the cap-and-ridge being attached around the periphery of said lens, the other of the cap-and-ridge being attached around the periphery of the semi-rigid anterior portion of said body, for releasably interconnecting said lens and the semi-rigid anterior portion of said body.

15. The anti-fog, interchangeable-lens goggle of claim 14, further comprising a latch depending from said body and operable between open and closed positions such that in the closed position the latch biases said lens onto the semi-rigid anterior portion of said body and thus reinforces the releasable interconnection of said lens and the semi-rigid anterior portion of said body, and in the open position of said latch said lens is released for removal from the semi-rigid anterior portion of said body.

\* \* \* \* \*